United States Patent [19]
Bovy et al.

[11] Patent Number: 5,106,834
[45] Date of Patent: Apr. 21, 1992

[54] LINEAR FREE-SULFHYDRYL-CONTAINING OLIGOPEPTIDE DERIVATIVES AS ANTIHYPERTENSIVE AGENTS

[75] Inventors: Philippe R. Bovy; Robert E. Manning; Joan M. O'Neal, all of St. Louis, Mo.

[73] Assignee: G. D. Searle & Co., Chicago, Ill.

[21] Appl. No.: 290,667

[22] Filed: Dec. 27, 1988

[51] Int. Cl.$^5$ .................. A61K 37/02; C07K 7/06
[52] U.S. Cl. ........................ 514/15; 514/13; 514/14; 530/328; 530/327; 530/326
[58] Field of Search ............. 530/328, 327, 326; 514/15, 14, 13

[56] References Cited

U.S. PATENT DOCUMENTS 4,496,554  1/1985  Wong ............................ 514/179
4,804,650  2/1989  Lewicki et al. ................. 514/15

FOREIGN PATENT DOCUMENTS 116784  12/1983  European Pat. Off.
223143  3/1986  European Pat. Off.

OTHER PUBLICATIONS

Baxter J. et al., *Biotechnology*, 6:529-546, May 1988.
A. J. deBold et al., *Life Sci.*, 28, 89-94 (1981).
Geller et al., *Biochem. Biophys. Res. Commun.*, 120 (2), 333-338 (1984).
Kangawa & Matsuo, *Biochem. Biophys. Res. Commun.*, 118 (1), 131-139 (1984).
Seidah et al., *Proc. Nat'l. Acad. Sci. USA*, 81, 2640-2644 (1984).
Yamanaka et al., *Nature* 309, 719-722 (1984).
Bush E. N. et al., *Fed. Proc* 45, 657 (1986).
R. Nutt, D. F. Veber, *Endocrin. Metab. Clin. North Am.*, 16, 19-41 (1988).
J. Tremblay et al., *FEBS Lett.*, 181, 17-22 (1985).
S. A. Waldman et al., *J. Biol. Chem.* 259, 14332-14334 (1984).
D. B. Shenck et al., *J. Biol. Chem.*, 260, 14887-14890 (1985).
D. C. Leitman et al., *J. Biol. Chem.*, 261, 11650-11655 (1986).
Suzuki et al., *2nd Annual Meeting of the American Society of Hypertension, Abstract* B60, 187 (1987).
G. M. Olins et al., *J. Cellular Biochem.*, Suppl. 12A, 20, (1988).
R. M. Scarborough et al., *J. Cellular Bioch.*, Suppl. 12A, 20, (1988).
Y. Kiso et al., *J. Protein Chem.*, 6, 147 (1987).
Y. Kiso et al., *Peptide Chemistry* 1987, 513, (1988).

*Primary Examiner*—Howard E. Schain
*Assistant Examiner*—Susan M. Perkins
*Attorney, Agent, or Firm*—J. Timothy Keane; Paul D. Matukaitis

[57] ABSTRACT

Synthesis and use of novel oligopeptides are described, many of which peptides contain one or several unnatural amino acids. These short linear peptide derivatives are characterized by the presence of a free sulfhydryl function. These compounds have a high affinity for the Atrial Natriuretic Peptide (ANP) receptor coupled to particulate guanylate cyclase. Such peptides are full agonists at the ANP receptor as demonstrated by the ability of the peptides to stimulate the production of cGMP and to relax smooth muscles in vitro. In accord with these observations, the compounds of the invention lower blood pressure in mammals. Preferred peptides are the following:
Cys-Cha-Gly-Gly-Arg-Ile-Asp-Arg-Ile-GlyNH$_2$; D-Cys-Cha-Gly-Gly-Arg-Ile-Asp-Arg-Ile-GlyNH$_2$; L-Pen-Cha-Gly-Gly-Arg-Ile-Asp-Arg-Ile-GlyNH$_2$; and Cys-Cha-Gly-Gly-Arg-Ile-Asp-Arg-IleNH$_2$.

14 Claims, 5 Drawing Sheets

FIG. 2 RELAXANT ACTIVITY OF RABBIT AORTA SMOOTH SMOOTH MUSCLE BY PEPTIDE NO. 2 AND ANP

FIG. 3 STIMULATION OF cGMP PRODUCTION IN RABBIT LUNG MEMBRANES BY PEPTIDE NO. 2 AND ANP

LINEAR FREE-SULFHYDRYL-CONTAINING OLIGOPEPTIDE DERIVATIVES AS ANTIHYPERTENSIVE AGENTS

FIELD OF THE INVENTION

This invention is in the field of cardiovascular therapeutics and relates to synthetic peptides or modified peptides useful for the control of hypertension. Of particular interest are short linear sulfur containing modified peptides which decrease mean arterial pressure in mammals. This effect is obtained by stimulation of the guanyl cyclase-coupled Atrial Natriuretic Peptide receptors for which these compounds are full agonists.

BACKGROUND OF THE INVENTION

Crude extracts of rat atria containing potent diuretic and natriuretic substances have been previously referred to as atrial natriuretic factor [A. J. deBold et al, *Life Sci.*, 28, 89-94 (1981)]. These substances have subsequently been chemically defined as peptides, commonly referred to as atrial natriuretic peptides or ANP.

Various peptides of related structures have been isolated, sequenced and shown to have natriuretic, diuretic and vasorelaxant activity in varying degrees. A group of atrial peptides of significant interest, known as Atriopeptins I, II and III (AP-I, AP-II and AP-III), are described, for example, in publication of Geller et al, *Biochem. Biophys. Res. Commun.*, 120 (2), 333-338 (1984), and in U.S. Pat. No. 4,496,554 to Needleman. These peptides are in the oxidized, that is, cyclized form, and have the following amino acid sequences:

ATRIOPEPTIN I or ANP-(103-123)

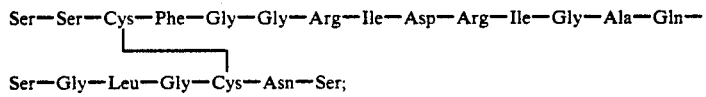

ATRIOPEPTIN II or ANP-(103-125):

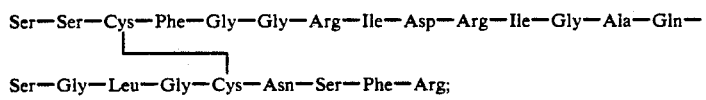

ATRIOPEPTIN III or ANP-(103-126):

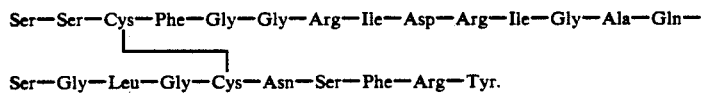

Various modifications of AP-III have also been described. Thus, the 28 amino acid peptide Ser-Leu-Arg-Arg-AP-III or ANP-(99-126), also known as Cardionatrin, is disclosed in European Patent Application 116,784, published Aug. 29, 1984. The human analogue of the 28 amino acid Cardionatrin I having a Met$^{110}$ replacement for Ile$^{110}$ is described by Kangawa and Matsuo, *Biochem. Biophys. Res. Commun.*, 118 (1), 131-139 (1984).

The 26 amino acid peptide Arg-Arg-AP-III, also known as atrial natriuretic factor or ANP-(101-126) is disclosed as a fragment of a larger 33 amino acid peptide by Seidah et al, *Proc. Nat'l. Acad. Sci. USA*, 81, 2640-44 (1984).

The 25 amino acid analog of AP-III having an Arg extension at the amino terminus, also known as auriculin, is described by Yamanaka et al, *Nature*, 309, 719-22 (1984).

Substitution of the Phe$^{106}$ residue with the unnatural cyclohexylalanine (Cha) in ANP-(103-126) peptidic hormone results in an increased potency in *Fed. Proc.*, 45, 657, (1986)]. Introduction of other non-proteinogenic amino acids like D-Cys or D-Ala has various effects on the activities and potency of the hormone. [(R. Nutt, D. F. Veber, *Endocrin. Metab. Clin. North. Am.*, 16, 19-41 (1988)]

The common designation "ANP" has been used for referring to any peptide of the family of atrial natriuretic peptides or atriopeptins. All of these peptides have a common amino acid sequence but may differ in length. The peptide sequences are designated according to the rule of the IUPAC-IUB Commission on Biochemical Nomenclature.

Atrial peptides have therapeutic potential in the treatment of congestive heart failure and hypertension and have been recognized as important for regulation of body fluid volume and blood pressure. Some of the physiological effects of atrial peptides are well-known. For example, ANP-(103-126) has a natriuretic and diuretic effect and it inhibits the contractile response of vascular smooth muscle to several agents. Also, ANP-(103-126) blocks angiotensin II-stimulated aldosterone secretion from the adrenal cortex and inhibits renin release. ANP-(103-126) acts through specific receptors at its target tissues. ANP-(103-126) induces activation of particulate guanylate cyclase and increases cyclic GMP formation [J. Tremblay et al, *FEBS Lett.*, 181, 17-22 (1985); S. A. Waldman et al, *J. Biol. Chem*, 259, 14332-14334 (1984)].

It has been suggested that cGMP mediates the effect of Atrial Natriuretic Peptide upon formation of the hormone-receptor complex. This conclusion is supported by the fact that ANP raises cGMP levels in various target tissues. [D. B. Shenck et al, *J. Biol. Chem.*, 260, 14887-14890 (1985)].

In fact, several studies using affinity labeling techniques [D. C. Leitman et al, *J. Biol. Chem.*, 261, 11650-11655 (1986)] suggest the existence of multiple ANP receptor sub-types. However, the relationship between multiple AP receptors and distinct physiological functions is not evident thus far.

Several publications report investigations of the biological activity of ANP fragments. In a series of publications [Suzuki et al, *2nd Annual Meeting of the American Society of Hypertension*, Abstract B60, 187 (1987), several analogues of ANP were reported to bind to the bovine aortic smooth muscle ANP receptors, but fail to elicit increase of cGMP.

Various linear fragments of rat and human ANP discriminate guanylate cyclase non-coupled ANP receptors from cyclase coupled receptors in rabbit lung membranes [G. M. Olins et al, *J. Cellular Biochem.*, Suppl. 12A, 20, (1988)], and from cultured vascular cells and isolated perfused kidneys [R. M. Scarborough et al. *J. Cellular Biochem.*, Suppl. 12A, 20, (1988)]. In particular, an octapeptide Phe-Gly-Gly-Arg-Ile-Asp-Arg-IleNH$_2$ binds to the bovine aortic smooth muscle ANP receptors but fails to elicit an increase of cGMP. EP Application No. 223,143, published May 27, 1987, describes a large class of several hundred peptides or modified peptides, a predominant number of which are characterized by inclusion of the pentapeptide sequence Arg-Ile-Asp-Arg-Ile. These peptides are mentioned as having high affinity for bovine aortic smooth muscle receptor sites. However, it is reported in EP Application No. 233,143 that these peptides lack the ability to stimulate the production of cGMP and have no vasorelaxant activity by themselves.

A linear, 15-amino acid peptide having the sequence Phe-Gly-Gly-Arg-Met-Asp-Arg-Ile-Gly-Ala-Gln-Ser-Gly-Leu-Gly has been described as having a dose-dependent natriuretic and diuretic effect but without hypotensive effects [Y. Kiso et al, *J. Protein Chem.*, 6, 147 (1987)].

Three peptides that are short fragments of ANP have been found to have a hypertensive action in the rat after a bolus injection [Y. Kiso et al, *Peptide Chemistry* 1987, 513, (1988)], namely, the peptides Phe-Gly-Gly-Arg-Leu-Asp; its cyclic analogue, cyclo (Phe-Gly-Gly-Arg-Leu-Asp); and Phe-Gly-Gly-Arg-Met-Asp-Arg-Ile-Gly None of the aforementioned publications describes a peptide of 16 or less amino acid residues mentioned to have the property of stimulating guanylate cyclase and cGMP production upon binding to the ANP receptor.

DESCRIPTION OF THE INVENTION

Figure 1:
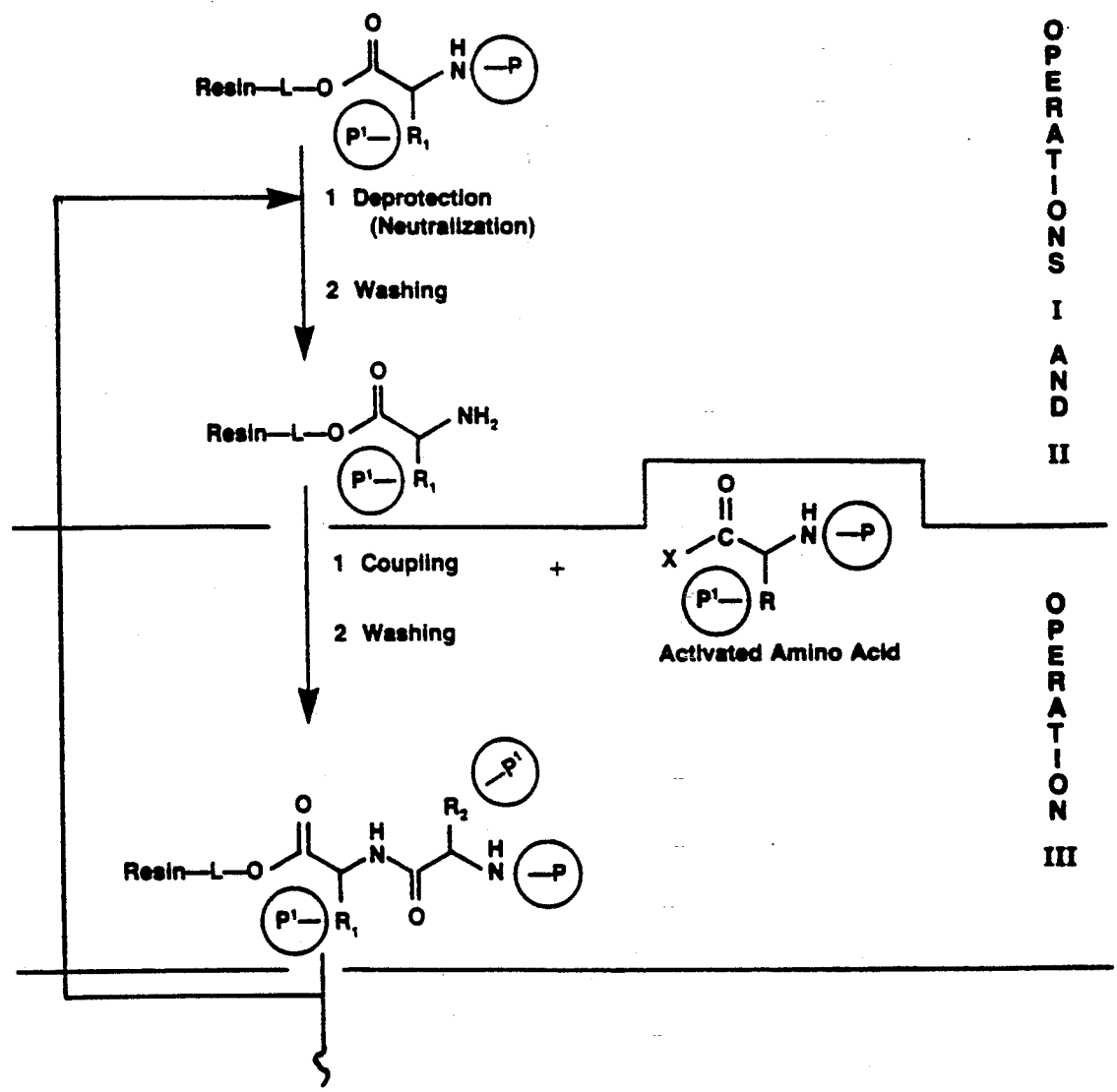
FIG. 1 is a schematic diagram of a general scheme for solid-phase synthesis of peptides of Formula I.
Figure 1:
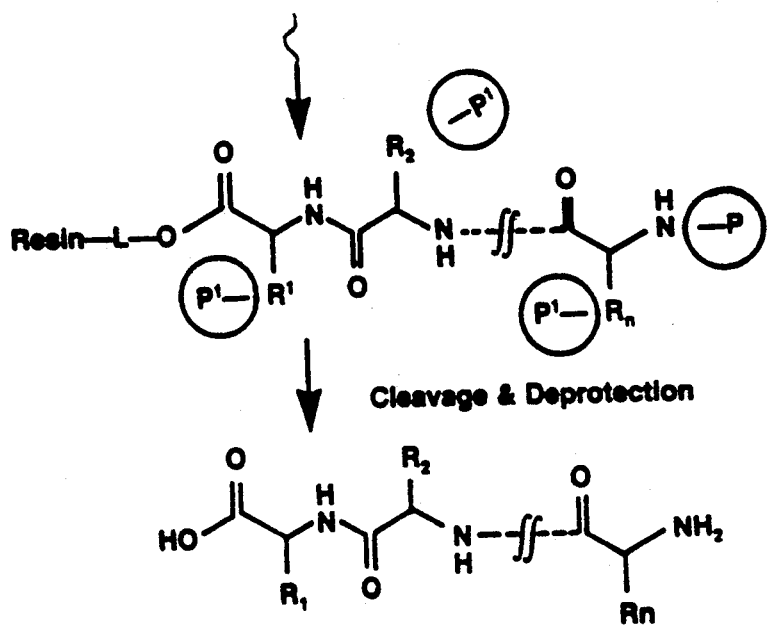

Treatment or control of hypertension is accomplished by administering to a mammal susceptible to hypertension a therapeutically effective amount of a compound from a class of linear peptide derivatives represented by Formula I $$X^1\text{-}Xaa^1\text{-}Xaa^2\text{-}Xaa^3\text{-}Xaa^4\text{-}Xaa^2\text{-}Xaa^3\text{-}X^3 \quad (I)$$

in which $X^1$ is a sulfur containing derivative of propionic acid capable of forming an amide bond with the amino group terminus of Xaa$^1$; Xaa$^1$ is an hydrophobic amino acid; $X^2$ is a dipeptide; Xaa$^2$ is a basic amino acid; Xaa$^3$ is an hydrophobic amino acid; Xaa$^4$ is an acidic amino acid; $X^3$ is the free carboxylic acid of the C-terminal of Xaa$^3$ or its pharmaceutically acceptable ester, amide or salt, or a glycine residue as the free acid or its pharmaceutically acceptable ester, amide or salt;

wherein the amino acid residues can be alpha or beta amino acids; with the proviso that the sum of all amino acids in a peptide derivative of Formula I is an integer in a range from 9 through 16.

Within Formula I there are seven subclasses of preferred compounds. The peptides of each of these seven subclasses are characterized in having a "core pentapeptide" defined as the sequence "Xaa$^2$-Xaa$^3$-Xaa$^4$-Xaa$^2$-Xaa$^3$".

A first subclass of preferred compounds of Formula I consists of those wherein the core pentapeptide is composed of the following amino acids:

Xaa$^2$ is a basic alpha amino acid independently selected from arginine, lysine, ornithine and homoarginine;

Xaa$^3$ is an alpha amino acid with a non-aromatic hydrophobic side chain independently selected from isoleucine, leucine, methionine and valine;

Xaa$^4$ is an acidic alpha amino acid selected from glutamic and aspartic acid;

More preferred are compounds within this first subclass wherein the Xaa$^3$ residues are methionine or isoleucine and the Xaa$^2$ residues are arginine. Even more preferred are compounds of Formula I wherein the "core pentapeptide" is the sequence Arg-Met-Asp-Arg-Ile. The most preferred compounds within this first subclass of Formula I are the compounds wherein the "core pentapeptide" is the sequence Arg-Ile-Asp-Arg-Ile composed of L-amino acids.

A second subclass of preferred compounds consists of those compounds where $X^1$ is selected from the following radicals:

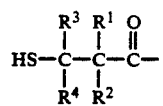

wherein each of $R^1$ and $R^2$ is independently selected from H, NH$_2$, NH—CO—Alkyl, NH—(Xaa)$_n$ where Xaa is selected from the alpha amino acids Ser, Leu and Arg and n is an integer selected from 1 through 6; wherein each of $R^3$ and $R^4$ is independently selected from H and alkyl, or $R^3$ and $R^4$ together may form a cyclic group. More preferred are compounds having a core pentapeptide selected from the following sequences Arg-Ile-Asp-Arg-Ile;
Arg-Met-Asp-Arg-Ile;
Arg-Ile-Glu-Arg-Ile;
Arg-Met-Glu-Arg-Ile; and
Lys-Ile-Asp-Arg-Ile.

A third subclass of preferred compounds of Formula I consists of those compounds wherein $X^2$ is a dipeptide selected from the amino acids glycine, L-alanine and D-alanine. More preferred are those compounds wherein the dipeptide fragment is Gly-Gly, Gly-Ala, Gly-D-Ala, Ala-Gly or D-Ala-Gly. The most preferred compounds have a Gly-Gly or a D-Ala-Gly fragment. More preferred are compounds having a core pentapeptide selected from the following sequences Arg-Ile-Asp-Arg-Ile;
Arg-Met-Asp-Arg-Ile;
Arg-Ile-Glu-Arg-Ile;
Arg-Met-Glu-Arg-Ile; and
Lys-Ile-Asp-Arg-Ile.

A fourth subclass of preferred compounds of Formula I consists of those compounds wherein $Xaa^1$ is an hydrophobic amino acid with a side chain selected from linear, branched, cyclic or polycyclic alkyl radicals of three to about fifteen carbon atoms, linear or branched alkyl radicals substituted by a phenyl ring or by a phenyl ring substituted with one or more groups selected from hydroxyl, alkyl, halo, alkoxy, alkylthio, alkylsufinyl and alkylsulfonyl. Of particular interest are those side chains selected from the following structures:

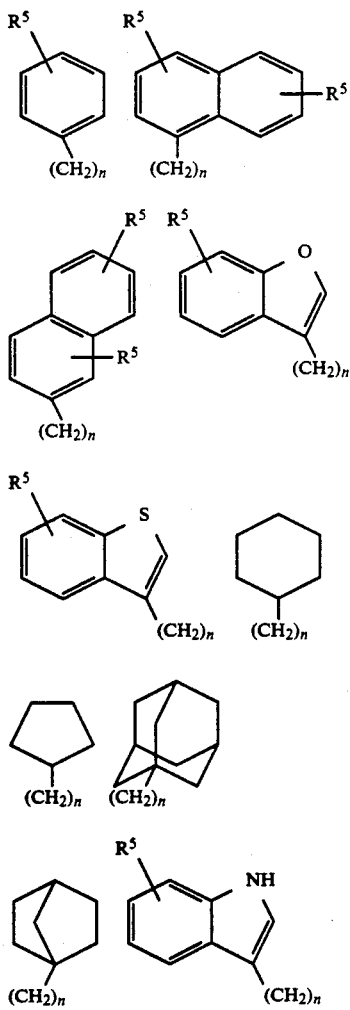

in which $R^5$ is selected from hydrido, hydroxyl, alkyl, halo, alkoxy, alkylthio, alkylsulfinyl and alkylsulfonyl, are compounds having a core pentapeptide selected from the following sequences Arg-Ile-Asp-Arg-Ile;
Arg-Met-Asp-Arg-Ile;
Arg-Ile-Glu-Arg-Ile;
Arg-Met-Glu-Arg-Ile; and
Lys-Ile-Asp-Arg-Ile.

Even more preferred are those compounds in which the residue $Xaa^1$ is an hydrophobic amino acid with an aromatic side chain. Still more preferred are those compounds of Formula I wherein $Xaa^1$ designates an hydrophobic amino acid containing no aromatic group. The most preferred compounds contain a lower linear, branched or cyclic alkyl radical of three to twelve carbon atoms. A particularly preferred amino acid for $Xaa^1$ is the L-cyclohexylalanine residue (abbreviated "Cha"):

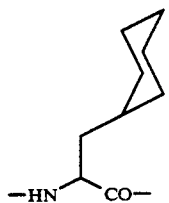

A fifth subclass of preferred compounds of Formula I consists of those compounds wherein $X^1$ is selected from the following radicals:

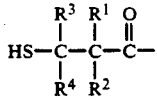

wherein each of $R^1$ and $R^2$ is independently selected from H, $NH_2$, NH—CO—Alkyl, NH—$(Xaa)_n$ where Xaa is selected from the alpha amino acids Ser, Leu and Arg and n is an integer selected from 1 through 6; wherein each of $R^3$ and $R^4$ is independently selected from H and alkyl, or $R^3$ and $R^4$ together may form a cyclic group; wherein $Xaa^1$ is an hydrophobic amino acid with a side chain which can be a linear or branched alkyl radical substituted by a phenyl ring or a phenyl ring substituted by one or more of hydroxyl, alkyl, halo and alkoxy; wherein $X^2$ is selected from the dipeptidic fragments Gly-Gly, Gly-Ala, Gly-D-Ala, Ala-Gly and D-Ala-Gly; wherein the core pentapeptide is selected from the following sequences Arg-Ile-Asp-Arg-Ile;
Arg-Met-Asp-Arg-Ile;
Arg-Ile-Glu-Arg-Ile;
Arg-Met-Glu-Arg-Ile; and
Lys-Ile-Asp-Arg-Ile.

wherein $X^3$ is selected from the free carboxylic acid of the C-terminal $Xaa^3$, its pharmaceutically acceptable ester, amide and salt, a glycine residue and its pharmaceutically acceptable ester, amide and salt. Even more preferred in this fifth subclass are these compounds wherein $X^1$ is a D- or L-cysteine or D- or L-penicillamine residue; wherein $X^2$ is selected from the dipeptidic fragments Gly-Gly, Gly-Ala, Gly-D-Ala, Ala-Gly and D-Ala-Gly; wherein the core pentapeptide is the sequence Arg-Ile-Asp-Arg-Ile; and wherein $X^3$ is selected from the free carboxylic acid of the C-terminal $Xaa^3$, its pharmaceutically acceptable ester amide and salt, a glycine residue and its pharmaceutically acceptable ester, amide and salt. Particularly preferred are the following compounds:

Cys-Phe-Gly-Gly-Arg-Ile-Asp-Arg-Ile-GlyNH$_2$;
D-Cys-Phe-Gly-Gly-Arg-Ile-Asp-Arg-Ile-GlyNH$_2$;
Cys-Phe-D-Ala-Gly-Arg-Ile-Asp-Arg-Ile-GlyNH$_2$;
Cys-Phe-Gly-Gly-Lys-Ile-Asp-Arg-Ile-GlyNH$_2$;
Cys-Phe-Gly-Gly-Arg-Met-Asp-Arg-Ile-GlyNH$_2$;
Cys-Phe-Gly-Gly-Arg-Ile-Glu-Arg-Ile-GlyNH$_2$;
Cys-Phe-Gly-Gly-Arg-Met-Glu-Arg-Ile-GlyNH$_2$;
Cys-Phe-Gly-D-Ala-Arg-Ile-Asp-Arg-Ile-GlyNH$_2$;
D-Pen-Phe-Gly-Gly-Arg-Ile-Asp-Arg-Ile-GlyNH$_2$;
L-Pen-Phe-Gly-Gly-Arg-Ile-Asp-Arg-Ile-GlyNH$_2$;
D-Cys-Phe-D-Ala-Gly-Arg-Ile-Asp-Arg-Ile-GlyNH$_2$;
D-Cys-Phe-Gly-Gly-Lys-Ile-Asp-Arg-Ile-GlyNH$_2$;
D-Cys-Phe-Gly-Gly-Arg-Met-Asp-Arg-Ile-GlyNH$_2$;
D-Cys-Phe-Gly-Gly-Arg-Ile-Glu-Arg-Ile-GlyNH$_2$;
D-Cys-Phe-Gly-Gly-Arg-Met-Glu-Arg-Ile-GlyNH$_2$;
D-Pen-Phe-Gly-Gly-Arg-Met-Asp-Arg-Ile-GlyNH$_2$; and
L-Pen-Phe-Gly-Gly-Arg-Met-Asp-Arg-Ile-GlyNH$_2$.

A sixth subclass of preferred compounds of Formula I consists of those compounds wherein $X^1$ is selected from the following radicals:

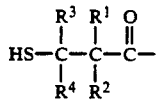

wherein each of $R^1$ and $R^2$ is independently selected from H, NH$_2$, NH—CO—Alkyl, NH—(Xaa)$_n$ where Xaa is selected from the alpha amino acids Ser, Leu and Arg and n is an integer selected from 1 through 6; wherein each of $R^3$ and $R^4$ is independently selected from H and alkyl, or $R^3$ and $R^4$ together may form a cyclic group; wherein $Xaa^1$ is an hydrophobic amino acid with a side chain which can be a linear, branched or cyclic alkyl radical of three to fifteen carbon atoms; wherein $X^2$ is selected from the dipeptidic fragments Gly-Gly, Gly-Ala, Gly-D-Ala, Ala-Gly and D-Ala-Gly; wherein the core pentapeptide is the sequence Arg-Ile-Asp-Arg-Ile; and wherein $X^3$ is selected from the free carboxylic acid of the C-terminal $Xaa^3$, its pharmaceutically acceptable ester, amide and salt, a glycine residue and it pharmaceutically acceptable ester, amide and salt. Even more preferred in this sixth subclass are those compounds wherein $X^1$ is a D- or L-cysteine or D- or L- penicillamine residue, wherein $X^2$ is selected from the dipeptidic fragments Gly-Gly, Gly-Ala, Gly-D-Ala, Ala-Gly and D-Ala-Gly; wherein the core pentapeptide is the sequence Arg-Ile-Asp-Arg-Ile, and wherein $X^3$ is selected from the free carboxylic acid of the C-terminal $Xaa^3$, its pharmaceutically acceptable ester, amide and salt, a glycine residue, and its pharmaceutically acceptable ester, amide and salt. Particularly preferred are the following compounds:

Cys-Cha-Gly-Gly-Arg-Ile-Asp-Arg-Ile-GlyNH$_2$;
D-Cys-Cha-Gly-Gly-Arg-Ile-Asp-Arg-Ile-GlyNH$_2$;
L-Pen-Cha-Gly-Gly-Arg-Ile-Asp-Arg-Ile-GlyNH$_2$;
Cys-Cha-Gly-Gly-Lys-Ile-Asp-Arg-Ile-GlyNH$_2$;
Cys-Cha-Gly-Gly-Arg-Met-Asp-Arg-Ile-GlyNH$_2$;
Cys-Cha-Gly-Gly-Arg-Ile-Glu-Arg-Ile-GlyNH$_2$;
Cys-Cha-Gly-Gly-Arg-Met-Glu-Arg-Ile-GlyNH$_2$;
Cys-Cha-D-Ala-Gly-Arg-Ile-Asp-Arg-Ile-GlyNH$_2$;
Cys-Cha-Gly-D-Ala-Arg-Ile-Asp-Arg-Ile-GlyNH$_2$;
D-Pen-Cha-Gly-Gly-Arg-Ile-Asp-Arg-Ile-GlyNH$_2$;
D-Cys-Cha-D-Ala-Gly-Arg-Ile-Asp-Arg-Ile-GlyNH$_2$
D-Cys-Cha-Gly-Gly-Lys-Ile-Asp-Arg-Ile-GlyNH$_2$;
D-Cys-Cha-Gly-Gly-Arg-Ile-Glu-Arg-Ile-GlyNH$_2$;
D-Cys-Cha-Gly-Gly-Arg-Met-Glu-Arg-Ile-GlyNH$_2$;
D-Pen-Cha-Gly-Gly-Arg-Met-Asp-Arg-Ile-GlyNH$_2$; and
L-Pen-Cha-Gly-Gly-Arg-Met-Asp-Arg-Ile-GlyNH$_2$.

A seventh subclass of preferred compounds of Formula I consists of those compounds wherein $X^1$ is a substituted 3-mercapto-propionic acid derivative, wherein $Xaa^1$ is an hydrophobic amino acid with a side chain which can be a linear, branched or cyclic alkyl radical of three to twelve carbon atoms; wherein $X^2$ is selected from the dipeptidic fragments Gly-Gly, Gly-Ala, Gly-D-Ala, Ala-Gly and D-Ala-Gly, wherein the core pentapeptide is the sequence Arg-Ile-Asp-Arg-Ile; and wherein $X^3$ is selected from the free carboxylic acid of the C-terminal $Xaa^3$, its pharmaceutically acceptable ester, amide and salt. Even more preferred in this seventh subclass are these compounds wherein X: is a D- or L-cysteine or D- or L-penicillamine residue; wherein $X^2$ is selected from the dipeptidic fragments Gly-Gly, Gly-Ala, Gly-D-Ala, Ala-Gly and D-Ala-Gly, wherein the core pentapeptide is the sequence Arg-Ile-Asp-Arg-Ile; and wherein $X^3$ is selected from the free carboxylic acid of the C-terminal $Xaa^3$, its pharmaceutically acceptable ester, amide and salt. Particularly preferred are the following compounds:

Cys-Cha-Gly-Gly-Arg-Ile-Asp-Arg-IleNH$_2$;
Cys-Cha-Gly-Gly-Lys-Ile-Asp-Arg-IleNH$_2$;
Cys-Cha-Gly-Gly-Arg-Met-Asp-Arg-IleNH$_2$;
Cys-Cha-Gly-Gly-Arg-Ile-Glu-Arg-IleNH$_2$;
Cys-Cha-Gly-Gly-Arg-Met-Glu-Arg-IleNH$_2$;
Cys-Cha-D-Ala-Gly-Arg-Ile-Asp-Arg-IleNH$_2$;
Cys-Cha-Gly-D-Ala-Arg-Ile-Asp-Arg-IleNH$_2$;
D-Pen-Cha-Gly-Gly-Arg-Ile-Asp-Arg-IleNH$_2$;
L-Pen-Cha-Gly-Gly-Arg-Ile-Asp-Arg-IleNH$_2$;
D-Cys-Cha-D-Ala-Gly-Arg-Ile-Asp-Arg-IleNH$_2$;
D-Cys-Cha-Gly-Gly-Lys-Ile-Asp-Arg-IleNH$_2$;
D-Cys-Cha-Gly-Gly-Arg-Met-Asp-Arg-IleNH$_2$;
D-Cys-Cha-Gly-Gly-Arg-Ile-Glu-Arg-IleNH$_2$;
D-Cys-Cha-Gly-Gly-Arg-Met-Glu-Arg-IleNH$_2$;
D-Pen-Cha-Gly-Gly-Arg-Met-Asp-Arg-IleNH$_2$; and
L-Pen-Cha-Gly-Gly-Arg-Met-Asp-Arg-IleNH$_2$.

An eighth subclass of preferred compounds of Formula I consists of those peptide derivatives embraced by Formula II:

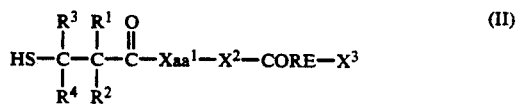

wherein each of $R^1$ and $R^2$ is independently selected from H, NH$_2$, NH—CO—Alkyl, NH—(Xaa)$_n$ where Xaa is selected from the alpha amino acids Ser, Leu and Arg and n is an integer selected from 1 through 6;

wherein each of R$^3$ and R$^4$ is independently selected from H and alkyl, or R$^3$ and R$^4$ together may form a cyclic group; wherein Xaa$^1$ is an hydrophobic amino acid with a side chain which can be a linear, branched, cyclic or polycyclic alkyl radicals of three to about fifteen carbon atoms, linear or branched alkyl radicals substituted by a phenyl ring or a phenyl ring substituted by one or more of hydroxyl, alkyl, halo, alkoxy, alkylthio, alkylsulfinyl and alkylsulfonyl groups; wherein X$^2$ is selected from the dipeptide fragments Gly-Gly, Gly-Ala, Gly-D-Ala, Ala-Gly and D-Ala-Gly; wherein CORE designates a core pentapeptide sequence selected from Arg-Ile-Asp-Arg-Ile, Arg-Met-Asp-Arg-Ile, Arg-Ile-Glu-Arg-Ile, and Lys-Ile-Asp-Arg-Ile; and, wherein X$^3$ is selected from the free carboxylic acid of the C-terminal Xaa$^3$, its pharmaceutically acceptable ester, amide and salt, a glycine residue and its pharmaceutically acceptable ester, amide and salt. Even more preferred in this eighth subclass are those compounds wherein X$^1$ is a D- or L-cysteine or D- or L- penicillamine residue; wherein Xaa$^1$ is selected from Phe, L-Cha and D-Cha; wherein X$^2$ is selected from the dipeptidic fragments Gly-Gly, Gly-Ala, Gly-D-Ala, Ala-Gly and D-Ala-Gly; wherein the core pentapeptide is the sequence Arg-Ile-Asp-Arg-Ile; and wherein X$^3$ is selected from the free carboxylic acid of the C-terminal Xaa$^3$, its pharmaceutically acceptable ester amide and salt, a glycine residue and its pharmaceutically acceptable ester, amide and salt. A preferred family of peptide derivative within the eighth subclass are the following compounds:

Cys-Phe-Gly-Gly-Arg-Ile-Asp-Arg-Ile-GlyNH$_2$;
D-Cys-Phe-Gly-Gly-Arg-Ile-Asp-Arg-Ile-GlyNH$_2$;
Cys-Cha-Gly-Gly-Arg-Ile-Asp-Arg-Ile-GlyNH$_2$;
Cys-Cha-Gly-Gly-Arg-Ile-Asp-Arg-IleNH$_2$;
Cys-Phe-Gly-Gly-Lys-Ile-Asp-Arg-Ile-GlyNH$_2$;
Cys-Phe-Gly-Gly-Arg-Met-Asp-Arg-Ile-GlyNH$_2$;
Cys-Phe-Gly-Gly-Arg-Ile-Glu-Arg-Ile-GlyNH$_2$;
Cys-Phe-Gly-Gly-Arg-Met-Glu-Arg-Ile-GlyNH$_2$;
Cys-Phe-D-Ala-Gly-Arg-Ile-Asp-Arg-Ile-GlyNH$_2$;
Cys-Phe-Gly-D-Ala-Arg-Ile-Asp-Arg-Ile-GlyNH$_2$;
D-Pen-Phe-Gly-Gly-Arg-Ile-Asp-Arg-Ile-GlyNH$_2$;
L-Pen-Phe-Gly-Gly-Arg-Ile-Asp-Arg-Ile-GlyNH$_2$;
D-Cys-Phe-D-Ala-Gly-Arg-Ile-Asp-Arg-Ile-GlyNH$_2$;
D-Cys-Phe-Gly-Gly-Lys-Ile-Asp-Arg-Ile-GlyNH$_2$;
D-Cys-Phe-Gly-Gly-Arg-Met-Asp-Arg-Ile-GlyNH$_2$;
D-Cys-Phe-Gly-Gly-Arg-Ile TM Glu-Arg-Ile-GlyNH$_2$;
D-Cys-Phe-Gly-Gly-Arg-Met-Glu-Arg-Ile-GlyNH$_2$;
D-Pen-Phe-Gly-Gly-Arg-Met-Asp-Arg-Ile-GlyNH$_2$;
L-Pen-Phe-Gly-Gly-Arg-Met-Asp-Arg-Ile-GlyNH$_2$;
Cys-Cha-Gly-Gly-Lys-Ile-Asp-Arg-Ile-GlyNH$_2$;
Cys-Cha-Gly-Gly-Arg-Met-Asp-Arg-Ile-GlyNH$_2$;
Cys-Cha-Gly-Gly-Arg-Ile-Glu-Arg-Ile-GlyNH$_2$;
Cys-Cha-Gly-Gly-Arg-Met-Glu-Arg-Ile-GlyNH$_2$;
Cys-Cha-D-Ala-Gly-Arg-Ile-Asp-Arg-Ile-GlyNH$_2$;
Cys-Cha-Gly-D-Ala-Arg-Ile-Asp-Arg-Ile-GlyNH$_2$;
D-Pen-Cha-Gly-Gly-Arg-Ile-Asp-Arg-Ile-GlyNH$_2$;
L-Pen-Cha-Gly-Gly-Arg-Ile-Asp-Arg-Ile-GlyNH$_2$;
D-Cys-Cha-D-Ala-Gly-Arg-Ile-Asp-Arg-Ile-GlyNH$_2$;
D-Cys-Cha-Gly-Gly-Lys-Ile-Asp-Arg-Ile-GlyNH$_2$;
D-Cys-Cha-Gly-Gly-Arg-Ile-Asp-Arg-Ile-GlyNH$_2$;
D-Cys-Cha-Gly-Gly-Arg-Ile-Glu-Arg-Ile-GlyNH$_2$;
D-Cys-Cha-Gly-Gly-Arg-Met-Glu-Arg-Ile-GlyNH$_2$;
D-Pen-Cha-Gly-Gly-Arg-Met-Asp-Arg-Ile-GlyNH$_2$;
L-Pen-Cha-Gly-Gly-Arg-Met-Asp-Arg-Ile-GlyNH$_2$;
Cys-Cha-Gly-Gly-Lys-Ile-Asp-Arg-IleNH$_2$;
Cys-Cha-Gly-Gly-Arg-Met-Asp-Arg-IleNH$_2$;
Cys-Cha-Gly-Gly-Arg-Ile-Glu-Arg-IleNH$_2$;
Cys-Cha-Gly-Gly-Arg-Met-Glu-Arg-IleNH$_2$;
Cys-Cha-D-Ala-Gly-Arg-Ile-Asp-Arg-IleNH$_2$;
Cys-Cha-Gly-D-Ala-Arg-Ile-Asp-Arg-IleNH$_2$;
D-Pen-Cha-Gly-Gly-Arg-Ile-Asp-Arg-IleNH$_2$;
L-Pen-Cha-Gly-Gly-Arg-Ile-Asp-Arg-IleNH$_2$;
D-Cys-Cha-D-Ala-Gly-Arg-Ile-Asp-Arg-IleNH$_2$;
D-Cys-Cha-Gly-Gly-Lys-Ile-Asp-Arg-IleNH$_2$;
D-Cys-Cha-Gly-Gly-Arg-Met-Asp-Arg-IleNH$_2$;
D-Cys-Cha-Gly-Gly-Arg-Ile-Glu-Arg-IleNH$_2$;
D-Cys-Cha-Gly-Gly-Arg-Met-Glu-Arg-IleNH$_2$;
D-Pen-Cha-Gly-Gly-Arg-Met-Asp-Arg-IleNH$_2$;
L-Pen-Cha-Gly-Gly-Arg-Met-Asp-Arg-IleNH$_2$;
Cys-Phe-Gly-Gly-Lys-Ile-Asp-Arg-IleNH$_2$;
Cys-Phe-Gly-Gly-Arg-Met-Asp-Arg-IleNH$_2$;
Cys-Phe-Gly-Gly-Arg-Ile-Glu-Arg-IleNH$_2$;
Cys-Phe-Gly-Gly-Arg-Met-Glu-Arg-IleNH$_2$;
Cys-Phe-D-Ala-Gly-Arg-Ile-Asp-Arg-IleNH$_2$;
Cys-Phe-Gly-D-Ala-Arg-Ile-Asp-Arg-IleNH$_2$;
D-Pen-Phe-Gly-Gly-Arg-Ile-Asp-Arg-IleNH$_2$;
L-Pen-Phe-Gly-Gly-Arg-Ile-Asp-Arg-IleNH$_2$;
D-Cys-Phe-D-Ala-Gly-Arg-Ile-Asp-Arg-IleNH$_2$;
D-Cys-Phe-Gly-Gly-Lys-Ile-Asp-Arg-IleNH$_2$;
D-Cys-Phe-Gly-Gly-Arg-Met-Asp-Arg-IleNH$_2$;
D-Cys-Phe-Gly-Gly-Arg-Ile-Glu-Arg-IleNH$_2$;
D-Cys-Phe-Gly-Gly-Arg-Met-Glu-Arg-IleNH$_2$;
D-Pen-Phe-Gly-Gly-Arg-Met-Asp-Arg-IleNH$_2$; and
L-Pen-Phe-Gly-Gly-Arg-Met-Asp-Arg-IleNH$_2$.

All compounds of Formula I are characterized in having a core peptidic sequence of amino acids which features the following pattern of physico-chemical properties: basic-hydrophobic-acidic-basic-hydrophobic. All compounds of Formula I are further characterized by the presence of a free-sulfhydryl-containing propionic acid derivative. Also, such free sulfhydryl-containing propionic derivative must be followed in the sequence by a hydrophobic amino acid residue. Furthermore, all compounds of Formula I are characterized as being linear peptidic compounds. Also, all compounds of Formula I are characterized in having from 9 to 16 amino acid residues.

Compounds of Formula I of particular interest are nano- and decapeptides containing cyclohexylalanine in their sequence. Also, such peptides are agonists at the receptor of Atrial Natriuretic Peptides which is an unexpected finding in view of the relatively short length of the Formula I peptides as compared to the circulating 28-mer hormone, Atrial Natriuretic Peptide.

Peptides of Formula I can be assembled from amino acids in the D- or L-optical isomer configuration. It is preferred that the peptides of this invention when assembled from proteinogenic amino acid residues have the natural (L-) configuration except when otherwise stated.

Compounds of Formula I are therapeutically useful in methods for treating hypertension by administering to a hypertensive patient a therapeutically-effective amount of a compound of Formula I. The phrase "hypertensive patient" means, in this context, a mammalian subject who suffers from the effects of hypertension or is susceptible to hypertensive conditions if not treated for such hypertensive conditions.

The phrases "free carboxylic acid of the C-terminal Xaa$^3$", "glycine residue", and the "pharmaceutically-acceptable ester, amide and salt" thereof, as used above, are exemplified by the following:

—COOH indicates a free carboxylic acid of the C-terminal Xaa³;

—COOR⁶ indicates an ester of the carboxylic acid of the C-terminal Xaa³;

—COO⁻M⁺ indicates a salt of the carboxylic acid of the terminal Xaa³;

—CONH₂, CONHR⁶, and CONR⁶R⁷; indicate amides of the carboxylic acid of the C-terminal Xaa³;

—COHNCH₂CO₂R⁶, —CONHCH₂CONHR⁶, —CONHCH₂CONR⁶R⁷, —CONHCH₂CONH₂ and indicate glycine residues;

wherein each of R⁶ and R⁷ is independently selected from linear branched and cyclic alkyl of one to about twelve carbon atoms, and M⁺ is a cation selected from Group IA metallic elements and Group IIA alkali and alkaline earth metallic elements.

The phrase "basic amino acids" embraces those residues in which the side chain has a positive charge at pH 6 or lower.

The phrase "acidic amino acids" embraces those residues in which the side chain has a negative charge at pH 6 or higher.

The phrase "hydrophobic amino acids" embraces those residues in which the side chain is a non-polar aliphatic or aromatic group that cannot form a hydrogen bond with water and which have little or no attraction for water molecules as compared with the strong hydrogen bonding which forms between water molecules.

The term "proteinogenic" described amino acids which are involved in the biological synthesis of naturally-occurring proteins.

Nomenclature used to define the peptide compounds of Formula I is that specified by the IUPAC [published in *European Journal of Biochemistry*, 138, 9–37 (1984)], wherein conventional representation of the peptides stipulates that in a peptide sequence the forms, it is the L form of the proteinogenic amino acid which is represented unless otherwise stated. Included within the Formula I compounds are all peptide derivatives diastereoisomers with chiral centers having stereo-configurations which are not otherwise specifically defined. In the amino acid structural formulas, each residue is generally represented by a single or 3-letter designation, corresponding to the trivial name of the amino acid in accordance with the following list:

| TRIVIAL NAME | SYMBOL | ONE-LETTER SYMBOL |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unspecified Amino Acid | Xaa | X |
| Cyclohexylalanine | Cha | — |
| Penicillamine | Pen | — |

DETAILED DESCRIPTION OF THE INVENTION

Peptides of Formula I can be synthesized by a suitable method, such as by exclusively solid-phase techniques, by partial solid-phase techniques, by fragment condensation or by classical solution addition. For example, the techniques of exclusively solid-phase peptide synthesis (SPPS) are set forth in the textbook "Solid-Phase Peptide Synthesis", Stewart & Young, 2nd Edition, *Pierce Chemical Company* (1984). The fragment condensation method of synthesis is exemplified in U.S. Pat. No. 3,972,859. Synthesis by the use of recombinant DNA techniques may also be used when no unnatural residues are present and should be understood to include the suitable employment of a structural gene coding for the desired form of analog. The synthetic peptide may be obtained by transforming a microorganism using an expression vector including a promoter and operator together with such structural gene and causing such transformed microorganism to express the peptide. A non-human animal may also be used to produce the peptide by gene-farming using such a structural gene. The synthetic peptide is then suitably recovered from the animal by extraction from sera or the like.

The peptides are preferably prepared using solid phase synthesis, such as that described by Merrifield, *J. Amer. Chem. Soc.*, 85, 2149 (1964), although other equivalent chemical syntheses known in the art can also be used as previously mentioned. Solid-phase synthesis is commenced from the carboxyl terminal end of the peptide by coupling a protected α-amino acid to a suitable resin. Such a starting material can be prepared by attaching α-amino protected amino acid residue to a suitably functionalized resin. See FIG. 1 which shows the general scheme for solid phase peptide synthesis.

Resins are commercially available from a variety of suppliers. The preparation of such a substituted resin is described by Stewart et al, "Solid Phase Peptide Synthesis".

Common to chemical preparation of the peptides of Formula I is the protection of the side chain groups of the various amino acid moieties with suitable protecting groups which will prevent a chemical reaction from occurring at that site until the group is ultimately removed. Usually also common is the protection of an alpha-amino protecting group to allow subsequent reaction to take place at that location. Accordingly, it is common that, as a step in the synthesis, an intermediate compound is produced which includes each of the amino-acid residues located in its desired sequence in the peptide chain with various of these residues linked to the side-chain protecting groups. In selecting a particular side chain protecting group to be used in the synthesis of the peptides, the following rules are followed: (a) the protecting group should be stable to the reagent and under the reaction conditions selected for removing the α-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain. Throughout the description herein, the term Ⓟ identifies a protecting group of the amino acid function, and Ⓟ' identifies a protecting group for a function on a s chain.

The α-amino protecting groups designated by Ⓟ are those known to be useful in the art in the step-wise synthesis of polypeptides. Among the classes of α-amino protecting groups represented by Ⓟ are: (1) acyl-type protecting groups, such as formyl, trifluoroacetyl, phthalyl, p-toluenesulfonyl (Tos), benzenesulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl (Z) and substituted Z, such as p-chlorobenzyloxycarbonyl (CBZ), p-nitrobenzyloxycarbonyl, p-bromobenzyloxycarbonyl, p-methoxybenzyloxycarbonyl; (3) aliphatic urethan-type protecting groups, such as t-butyloxycarbonyl (Boc), diisopropylmethoxycarbonyl, isopropyloxycarbonyl, ethoxycarbonyl, allyloxycarbonyl; (4) cycloalkyl urethan-type protecting groups, such as fluorenylmethyloxycarbonyl (Fmoc), cyclopentyloxycarbonyl, adamantyloxycarbonyl, and cyclohexyloxycarbonyl; (5) thiourethan-type protecting groups, such a phenylthiocarbonyl; (6) alkyl-type protecting groups, such as triphenylmethyl (trityl), benzyl (Bzl); (7) trialkylsilane groups, such as trimethylsilane. The preferred α-amino protecting group is Boc.

When Ⓟ' is a protecting group for the hydroxyl group of Ser, Ⓟ' is preferably selected from the class consisting o -1 (Ac), benzoyl (Bz), tert-butyl, trityl, tetrahydropyranyl, benzyl ether (Bzl), 2,6-dichlorobenzyl and Z. The most preferred protecting group is Bzl. Ⓟ' can be H, which means there is no protect on the hydroxyl group.

When Ⓟ' is a protecting group for Cys, Ⓟ' is preferably selected from the class consisting of p-methoxybenzyl (MeOBzl), p-methylbenzyl, thioethyl, acetamidomethyl, trityl and Bzl. The most preferred protecting group is acetamidomethyl. Ⓟ' can also be H, meaning that there is no protecting group on the sulfur.

When Ⓟ' is a protecting group for the guanidino group of arg, Ⓟ' is preferably selected from the class consisting of H, nitro, Tos, Z, adamantyloxycarbonyl and Boc. Tos is most preferred.

When Ⓟ' is H, or an ester-forming protecting group the β-carboxyl group of Asp, Ⓟ' is preferably selected from the class consisting of Bzl, 2,6-dichlorobenzyl (Dcb), CBZ, methyl and ethyl. Bzl is most preferred.

When Ⓟ' is H, or a protecting group for the amido group of Gln or Asn, in Ⓟ' latter case is preferably xanthyl (Xan).

The protecting group for carboxyl terminus is selected from the class consisting of OH, OCH$_3$, amides, hydrazides and esters, including an amide, a benzyl ester and a hydroxymethyl ester anchoring bond used in solid phase syntheses for linking to a solid resin support, such resin support exemplified by the following:

—NH-benzhydrylamine (BHA) resin support,
—NH-paramethylbenzhydrylamine (MBHA) resin support,
—NH-paramethoxybenzylhydryl-amine resin support,
—O—CH$_2$-polystyrene resin support,
—O—CH$_2$-benzyl-polystyrene resin support,
—O—CH$_2$-phenylacetamidomethyl-polystyrene resin support, and
—O—CH$_2$-phenyl-oxymethyl resin support.

The polystyrene polymer is preferably a copolymer of styrene with about 0.5 to 2% divinyl benzene as a cross-linking agent, such that the polystyrene polymer is completely insoluble in certain organic solvents.

The procedure leading to the growth of the peptide chain is exemplified herebelow for a procedure using the t-butyloxycarbonyl group as the protective group for the amino function of the amino acid. See also the general scheme for SPPS in FIG. 1.

Following the coupling of the t-Boc protected amino acid to the resin support, the α-amino protecting group is removed, as by using trifluoroacetic acid (TFA) in methylene chloride (CH$_2$Cl$_2$), TFA alone or with HCl in dioxane. Preferably 50 volume % TFA in methylene chloride is used. The deprotection is carried out at a temperature between about 0° C. and room temperature. Other standard cleaving reagents and conditions for removal of specific α-amino protecting groups may be used as described in Schroder & Lubke, "The Peptides", *Academic Press*, 1, 72–75 (1965).

After removal of the α-amino protecting group of the first α-amino acid, the remaining α-amino- and side chain-protected amino acids are coupled step-wise in the desired order to obtain the intermediate compound defined hereinbefore. As an alternative to adding each amino acid separately in the synthesis, some of the amino acids may be coupled to one another prior to addition to the solid phase reactor. The selection of an appropriate coupling reagent is within the skill of the art. Particularly suitable as coupling reagents are N,N'-dicyclohexylcarbodiimide (DCC) and N,N'-diisopropylcarbodiimide (DIC).

Activating reagents compatible with the routine operations of the solid phase synthesis of the peptides are well known in the peptide art. Examples of suitable activating reagents are: (1) carbodiimides, such as N,N'-diisopropyl carbodiimide, N-ethyl-N'-(3-dimethylaminopropyl)carbodiimide; (2) cyanamides such as N,N'-dibenzylcyanamide; (3) ketenimines; (4) isoxazolium salts, such as N-ethyl-5-phenyl isoxazolium-3'-sulfonate; (5) monocyclic nitrogen-containing heterocyclic amides of aromatic character containing one through four nitrogen atoms in the ring, such as imidazole, pyrazole, and 1,2,4-triazole derivatives. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) nitrogen-containing heterocyclic compounds having a hydroxy group on one ring nitrogen, such as N-hydroxyphthalimide, N-hydroxysuccinimide and 1-hydroxybenzotriazole (HOBt). Other activating reagents and their use in peptide coupling are described in Schroder & Lubke, in Chapter III, (vide supra) and by Kapoor, *J. Phar. Sci.*, 59, 1–27 (1970).

Each protected amino acid or amino acid sequence is introduced into the solid phase reactor in about a two-to-ten fold excess, and the coupling is carried out in a medium of dimethylformamide DMF:CH$_2$Cl$_2$ or in DMF or CH$_2$Cl$_2$ alone. In instances where the coupling is carried out manually, the success of the coupling reaction at each stage of the synthesis is monitored by the ninhydrin reaction, as described by E. Kaiser et al, *Anal. Biochem.*, 34, 595 (1970). In cases wherein incomplete coupling occurs, the coupling procedure is repeated before removal of the α-amino protecting group prior to the coupling of the next amino acid. The coupling reactions can be performed automatically, as for example on Applied Biosystems Inc. model 430A peptide synthesizer.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups with the exception of ACM.

As an alternative route, the intermediate peptide may be separated from the resin support by alcoholysis after which the recovered carboxyl terminal ester is converted to the acid by hydrolysis or to the amide by ammonolysis. Any side chain protecting groups may then be cleaved as previously described or by other known procedures, such as by catalytic reduction (e.g. Pd on $BaSO_4$). When using hydrogen fluoride for cleavage, anisole and 2-mercaptopyridine are included in the reaction vessel for scavenging. In cases where anhydrous HF is harmful for the peptide, a much more labile protecting group can be used for the synthesis.

Such systems are provided, among others, by other resins used with Bpoc, Fmoc, or Nps protected amino acids.

EXAMPLE I

Peptide No. 1 Cys-Phe-Gly-Gly-Arg-Ile-Asp-Arg-Ile-GlyNH$_2$, was prepared by solid phase synthesis on a 4-methylbenzhydrylamine resin substituted with t-Boc-Gly (substitution range: 0.3 to 0.5 mmol/g). The amino-acid derivatives used to assemble the peptide were chosen from the following list: t-Boc-L-Cys(Acm), t-Boc-L-Phe, t-Boc-Gly, t-Boc-L-Arg(Tos), t-Boc-L-Ile, t-Boc-L-Asp(OBzl), (commercially available from Peptide International Inc. and/or Peninsula Laboratories and/or Applied Biosystems, Inc.). Characterization of the peptides include amino acids analysis (Beckman 6300HPA), sequencing (Applied Biosystem Protein Sequences 620) and FAB mass spectroscopy.

Synthesis Procedure

Peptide No. 1 was synthesized by automated machine synthesis (Applied Biosystems Inc. Model 430A Peptide Synthesizer) utilizing the standard protocols described in the Applied Biosystems Inc. System Software Version 1.30.

Cleavage and Deprotection Procedures

The dried, TFA deprotected peptide resin (1 g, 0.3–0.5 mmol/g), anisole (1 g) and 2-mercaptopyridine (0.4 g) were stirred at 0° C. in liquid HF (10–15 ml) in a standard Teflon vessel for 1½ hours. The HF was evaporated and the residue was triturated in diethylether (4×40 ml), ethyl acetate (4×40 ml), and extracted with 80% acetic acid (AcOH) (3×30 ml) by filtration. The filtrate was concentrated to 5 ml volume with a rotary evaporator at 5°–10° C. @ 1 mm Hg. The residue was redissolved in water containing 0.05% TFA and lyophilized.

Purification Procedure

The above solution was filtered through a Whatman 934 AH glass fiber filter and was applied to a chromatography column (50×300 mm) packed with 200 g of Vydac C18 silica (Vydac 218TPB 15–20; 30 mμ pore size). The column was eluted at a flow of 8 ml/min., first with 5% acetonitrile in water containing 0.05% TFA followed by a 2 hour gradient from 5 to 40% acetonitrile in water containing 0.05% TFA while collecting fractions. The product usually eluted after 1 hour of the gradient indicated by monitoring the flow by UV at 220nM. The peptide-containing fractions were analyzed by analytical HPLC. Those fractions determined to be greater than 85% pure were combined. The peptide was obtained in homogeneous form by semi-preparative HPLC on a Vydac C18 column (218TP510, i.d. 10 mm, length 25 cm, 5 micron particle size) using a linear gradient of 15 to 35% acetonitrile in 0.05% trifluoroacetic acid at a flow rate of 4 ml/min. Homogeneity of the collected fractions was determined by analytical HPLC.

Removal of the Acm Protecting Group

To a magnetically stirred solution of 100 mg of the material prepared above, in 20 ml $H_2O$, are added 200 mg of $Hg(OAc)_2$. The pH of the solution is adjusted to 4 with acetic acid, while stirring at 25° C., $H_2S$ is bubbled through the reaction mixture. After 20 min., the black precipitate of HgS is removed by filtration through a pad of celite and the peptide is obtained as a solid by lyophilization of the filtrate.

The purity of the compound is checked by analytical HPLC and characterized by FAB Mass Spectroscopy: the isotope pattern (M+H) cluster is observed at the expected value 1092.5.

Amino acid analysis (Theoretical, found): Asp(1,1.07), Gly(3,3.17), Ile(2,2.00), Phe(1,1.00), Arg(2,2.00).

This free sulfhydryl containing peptide is sensitive to air oxidation. If it must be dissolved in a solvent, the solvent should be deoxygenated and the pH of the solution kept acidic (pH of about one to five).

EXAMPLE 2 THROUGH 7 GENERAL PROCEDURE

Peptides No. 2–7 were prepared by solid phase synthesis on a 4-methylbenzhydrylamine resin (p-MBHA, 1% cross-linked polystyrene/divinylbenzene, 200-400 mesh) substituted with 0.3 to 0.5 meq/g of t-Boc-Gly or t-Boc-L-Ile. The amino acid derivatives utilized to assemble the peptide chain include: t-Boc-Cha, t-Boc-Ser(Bzl), t-Boc-Cys(Acm), t-Boc-Phe, t-Boc-D-Cys(Acm), t-Boc-Gly, t-Boc-Agg(Tos), t-Boc-Ile, t-Boc-Asp(OBzl), t-Boc-Ala, t-Boc-L-Pen (4-Me-Bzl), t-Boc-D-Cys(4-Me-Bzl), t-Boc-Leu commercially available from Peptide International, Inc. and/or Peninsula Laboratories and/or Applied Biosystems, Inc. All reagents and solvents were ACS reagent grade or conformed to USP standard defined in the U.S. Pharmacopeia. The deprotection, cyclization and purification procedures were similar generally to the procedures described above for Peptide No. 1.

Synthesis Procedure

5 The peptides were synthesized by automated machine synthesis or by manual synthesis. In the case of automated machine synthesis, an Applied Biosystems Inc. Peptide Synthesizer (model 430A) was used and the synthetic steps were performed according to the standard protocols described in the Applied Biosystems Inc. System Software Version 1.30.

In the case of the manual synthesis, the peptide chain was assembled by a procedure based on repetition of the following three operations (multiple couplings were performed when necessary):

| Operation | Step | Reagents | No. Times | Mix Time (min.) |
|---|---|---|---|---|
| I | | DEPROTECTION | | |
| | 1 | $CH_2Cl_2$* | 3 | 1 |
| | 2 | Prewash w/50% trifluoroacetic acid (TFA)/$CH_2Cl_2$ | 1 | 1 |
| | 3 | Deprotect w/50% TFA/$CH_2Cl_2$ | 1 | 30 |
| | 4 | $CH_2Cl_2$ | 3 | 1 |
| | 5 | Isopropanol | 2 | 1 |
| | 6 | $CH_2Cl_2$ | 5 | 1 |
| | 7 | Kaiser Test | | |
| II | | NEUTRALIZATION | | |
| | 1 | 5% diisopropylethylamine/$CH_2Cl_2$ | 2 | 2 |
| | 2 | $CH_2Cl_2$ | 3 | 1 |
| III | | COUPLING | | |
| | 1 | swell resin with $CH_2Cl_2$/DMF; | 3 | 1 |
| | 2 | Boc-aa (4–10 eq.)/$CH_2Cl_2$/DMF; | 3 | 0.5 |
| | 3 | 4–10 eq. of 1M DCC/$CH_2Cl_2$ | 1 | 120 |
| | 4 | $CH_2Cl_2$ | 2 | 1 |
| | 5 | Ethanol | 1 | 1 |
| | 6 | $CH_2Cl_2$ | 3 | 1 |

Peptide No. 2

Peptide No. 2 having the formula Cys-Cha-Gly-Gly-Arg-Ile-Asp-Arg-Ile-GlyNH$_2$ was synthesized using the automated procedure and isolated as described in the peptide synthesis section.

FAB Mass Spectroscopy: the isotope pattern (M+H) cluster is observed at the expected value 1098.5.

Amino acid analysis (Theoretical, found): Asp(1., 1.11), Gly(3, 2.93), Ile(2, 1.70), Arg(2, 1.84), Cha(1, 0.67).

Peptide No. 3

Peptide No. 3 having the formula (D-Cys)-Phe-Gly-Gly-Arg-Ile-Asp-Arg-Ile-GlyNH$_2$ was synthesized using the manual procedure and isolated as described in the peptide synthesis section.

Amino acid analysis (Theoretical, found) Asp(1, 1.00), Gly(3, 3.16), Ile(2, 1.99), Phe(1, 0.97), Arg(2, 1.96).

Peptide No. 4

Peptide No. 4 having the formula Cys-Phe-(D-Ala)-Gly-Arg-Ile-Asp-Arg-Ile-GlyNH$_2$ was synthesized using the manual procedure and isolated as described in the peptide synthesis section.

Amino acid analysis (Theoretical, found) Asp(1, 1.04), Gly(2, 1.94), Ile(2, 1.91), Phe(1, 0.97), Arg(2, 2.09), Ala(2, 1.02).

Peptide No. 5

Peptide No. 5 having the formula (D-Cys)-Cha-Gly-Gly-Arg-Ile-Asp-Arg-Ile-GlyNH$_2$ was synthesized using the automated procedure and isolated as described in the peptide synthesis section.

FAB Mass Spectroscopy: the isotope pattern (M+H) cluster is observed at the expected value 1098.6.

Amino acid analysis (Theoretical, found) Asp(1, 1.03), Gly(3, 2.94), Ile(2, 1.81), Cha(1, 0.77), Arg(2, 1.98).

Peptide No. 6

Peptide No. 6 having the formula (L-Pen)-Cha-Gly-Arg-Ile-Asp-Arg-Ile-Gly-NH$_2$ was synthesized using the automated procedure and isolated as described in the peptide synthesis section.

FAB Mass Spectroscopy: the isotope pattern (M+H) cluster is observed at the expected value 1127.

Amino acid analysis (Theoretical, found) Asp(1, 0.98), Gly(3, 3.13), Ile(2, 1.83), Cha(1, 0.62), Arg(2, 1.95).

Peptide No. 7

Peptide No. 7 having the formula Cys-Cha-Gly-Gly-Arg-Ile-Asp-Arg-IleNH$_2$ was synthesized using the automated procedure and isolated as described in the peptide synthesis section. FAB Mass Spectroscopy: the isotope pattern (M+H) cluster is observed at the expected value 1041.3.

Amino acid analysis (Theoretical, found); Asp(1, 0.94), Gly(2, 2.16), Ile(2, 2.05), Cha(1, 0.84), Arg(2, 1.92).

BIOLOGICAL EVALUATION

Peptides No. 1 through 7 were evaluated for their biological activity. The biological assays used to evaluate the compounds are listed below and then described in greater detail thereafter:

A Competitive binding using a particulate rabbit lung membrane preparation;
B. Vasorelaxant activity using rabbit aortic rings;
C. cGMP production in isolated rat or rabbit aorta and rabbit lung membranes;
D. Effect on arterial blood pressure when administered to anesthetized rats.

A. Competitive Binding Experiments on Isolated Rabbit Lung Membrane

Preparation of rabbit lung membranes—The procedure was carried out at 4° C. Frozen rabbit lung lobes (Pel-Freez, Rogers, AR) were minced and then homogenized for 30 sec. with a Brinkmann Polytron in 5 volumes of a solution containing 0.25 M sucrose, 3 mM $MgCl_2$, 1 mM EDTA and 5 mM Tris pH 7.5. The homogenate was filtered through cheesecloth to remove some fat and connective tissue and the filtrate was centrifuged at 5,000×g for 20 min. The supernatant was centrifuged at 100,000×g for 90 min. The washed pellet was suspended in 50 mM Tris pH 7.5 at a final concentration of 4 mg/ml. The Biorad protein assay kit was used to assay membrane protein. The rabbit lung membrane preparation was stored in aliquots at −80° C. and was stable for at least 2 months. The binding assay utilized 0.25 ml of a solution containing 50 mM Tris pH 7.5, 0.1% bovine serum albumin, 100 μg membrane protein and $^{125}$I-ANP-(103–126) (2–3×10$^4$ cpm; specific activity of about 740 Ci/mmol) in the absence or presence of unlabelled peptide The reaction was initiated by the addition of membranes and the mixture was incubated at 25° C. for 30 min. The incubation was terminated with 4 ml ice-cold 50 mM Tris pH 7.5 and the mixture was filtered to separate membrane-bound labelled peptide from free ligand using a PHD Cell Harvester (Cambridge Technology, Inc., Mass.). The incubation tube and filter were washed with ice-cold buffer. Filters were assayed for radioactivity in a Micromedic gamma counter. Nonspecific binding was defined as binding in the presence of 10$^{-6}$ M unlabelled ANP-(103–126). Specific binding was calculated as total binding minus nonspecific binding. Binding data were analyzed by a nonlinear least-squares curve fitting program.

It was previously found that the rabbit lung contains a large number of specific binding sites for ANP, presumably consisting of a single class of high affinity receptors, as indicated by a linear Scatchard plot [G. M. Olins et al, *Biochem. Biophys. Res. Commun.*, 140, 302-307 (1987)]. However, it has now been discovered that some analogues of ANP are able to discriminate between receptor subtypes.

Competitive binding studies and affinity cross-linking experiments using a linear ANP analog revealed the presence of two populations of ANP binding sites, a small proportion (approximately 27%) of which are linked to guanylate cyclase activity. [G. M. Olins et al., *J. Biol. Chem.*, 263 (10989) 1988]. Binding of ANP analogs to the cyclase-linked receptors correlates with smooth muscle relaxant activity. For convenience, this receptor subclass is referred to as the vasorelaxant (VR) receptor. The other population of high affinity binding sites (approximately 73%) is not associated with guanylate cyclase or vasorelaxant activity and so are termed nonvasorelaxant (NVR) binding sites. The peptides of this invention bind to the two sites with some selectivity as can be seen from Table II. Peptides of Formula I possess the dual advantage of having a relatively short linear sequence as compare to naturally occurring ANP, while having a relatively high binding affinity to the VR receptor. The ability of the peptides of Formula I to elicit full biological response and thus to act as a full agonist is shown by the results in the rabbit aorta ring relaxation assay.

B. Vasorelaxant Activity Using Rabbit Aortic Rings

Figure 2:
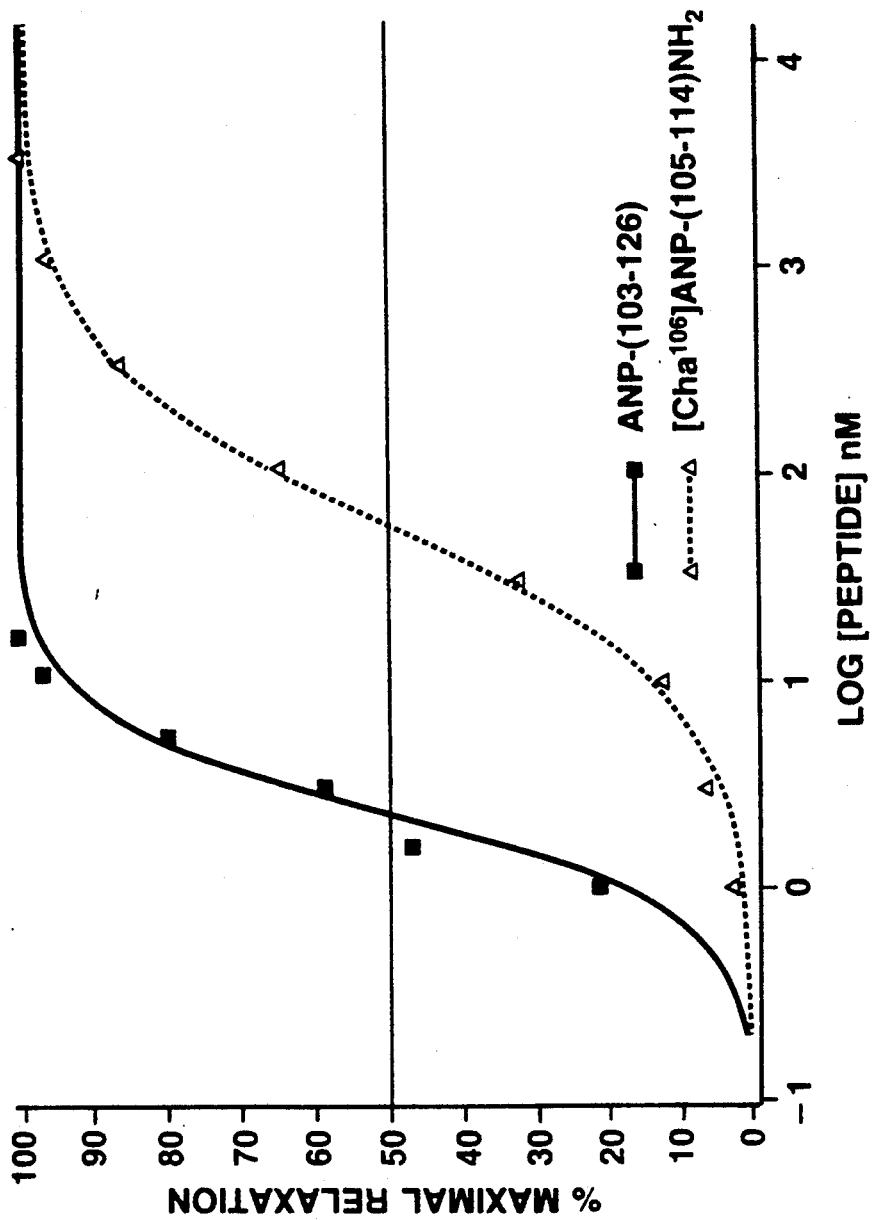
FIG. 2 shows concentration response curves for ANP-(103-126) and for Peptide No. 2 [Cha$^{106}$]ANP-(103-114)NH$_2$ in isolated rabbit aorta.

A typical dose response curve for the relaxation of the rabbit aorta ring by Peptide 2 of the invention is shown in FIG. 2. It can be seen that this compound with only ten amino acid residues was a full agonist with about one twenty-fifth the potency of ANP-(103-126) which has twenty-four amino acids. From Table II, it can be seen that this activity is also found in all the peptides of this invention, although with various degrees of potency. One nanopeptide (Peptide 7) has about one sixtieth the potency of the ANP-(103-126).

TABLE II

| # | Sequence | Relative Potencies to ANP-(103-126)* | | |
|---|---|---|---|---|
| | | Binding NVR | VR | Rabbit Aorta |
| 1 | CFGGRIDRIG-NH$_2$ | 0.81 | 0.0012 | |
| 2 | CZGGRIDRIG-NH$_2$ | 0.36 | 0.013 | 0.038 |
| 3 | X$^1$FGGRIDRIG-NH$_2$ | | | 0.015 |
| 4 | CFX$^2$GRIDRIG-NH$_2$ | 0.48 | 0.002 | |
| 5 | X$^1$ZGGRIDRIG-NH$_2$ | | | 0.018 |
| 6 | X$^3$ZGGRIDRIG-NH$_2$ | | | 0.010 |
| 7 | CZGGRIDRI-NH$_2$ | | | 0.015 |

*apparent K$_i$ of the standard in the binding assay is 0.25 ± 0.16 nM and EC$_{50}$ in the rabbit aorta is 2.3 ± 1.6 nM (n = 8)
Z = Cha; X$^1$ = D-Cys; X$^2$ = D-Ala; X$^3$ = L-Pen.

Rabbit Aorta Vasorelaxant Activity Assay Procedure

Male New Zealand White rabbits (2-2.5 kg) were sacrificed using an overdose of pentobarbital. The thoracic aorta was removed, cleaned of adherent fat and connective tissue and then cut transversely into 3 mm ring segments. The endothelium was removed from the rings by gently sliding a rolled-up piece of filter paper into the vessel lumen. The rings were then mounted in a water-jacketed tissue bath, maintained at 37° C., between a moveable and fixed stainless steel wire, with the moveable end attached to an FT03 Grass transducer coupled to a Model 7D Grass Polygraph for recording isometric force responses. The bath was filled with 20 mL of oxygenated (95% oxygen/5% carbon dioxide) Krebs solution of the following composition (mM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one g of passive tension was placed on the rings. Norepinephrine (NE) was then added to the bath to achieve a final concentration of 50 nM and when the isometric tension response had reached a plateau level, the test peptide was added to the bath cumulatively (every 10 min) until relaxation back to the baseline was achieved. A plot of log [peptide] vs % relaxation was then used to calculate the EC$_{50}$ value for each test peptide. These values were then compared to the EC$_{50}$ response for the standard [ANP-(103-126)] which was obtained from concentration-response data measured in an identical ring segment from the same rabbit. Each test peptide was evaluated in aortae from two rabbits.

C. cGMP Production

The vasorelaxant activity of the peptide of the invention has been correlated to ability of the peptide to stimulate cGMP production in various tissues and species, as follows:

C1—Effect of ANP-(103-126) and Peptide No. 2 on Guanylate Cyclase Activity

Figure 3:
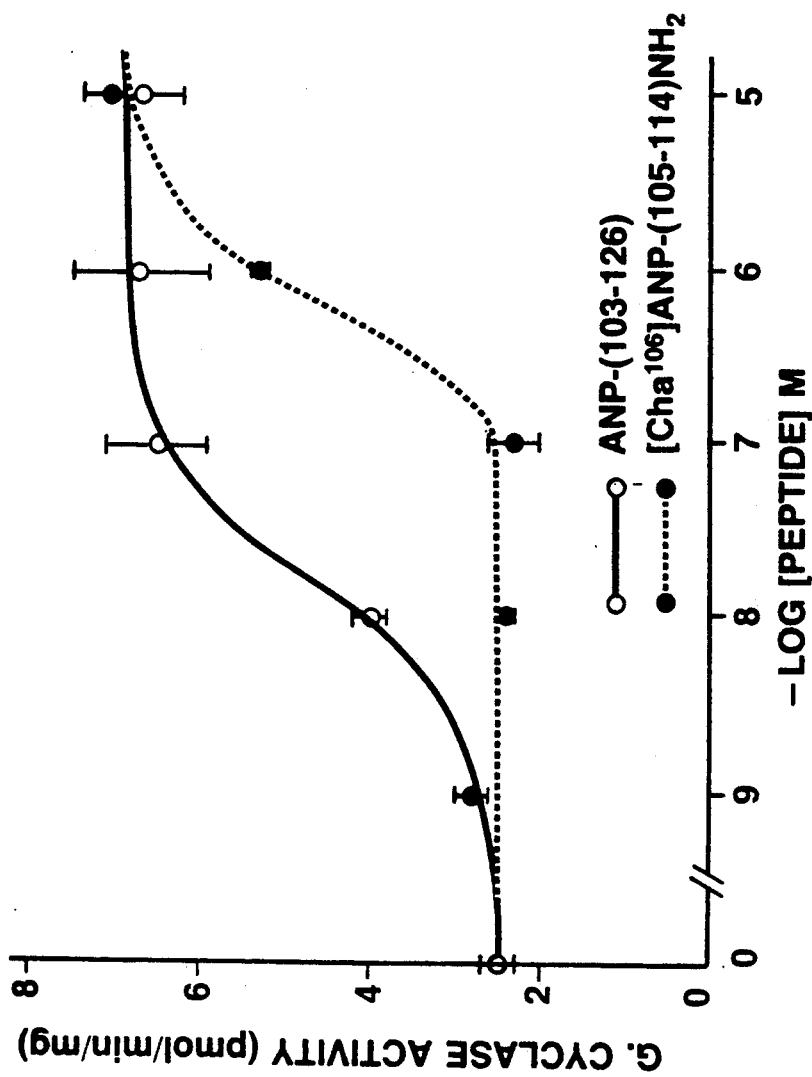
FIG. 3 shows stimulation of rabbit lung membrane particulate guanylate cyclase activity by ANP-(103-126) and by Peptide No. 2 [Cha$^{106}$]ANP-(105-114)NH$_2$.

Atrial peptides stimulate particulate guanylate cyclase activity in various tissue preparations [S. A. Waldman et al, *J. Biol. Chem.*, 259, 14332-4 (1984). The effects of ANP-(103-126) and Peptide No. 2 on the particulate guanylate cyclase activity in rabbit lung membranes is illustrated in FIG. 3. Stimulation of rabbit lung particulate guanylate cyclase activity by the Decapeptide 2 and ANP-(103-126) occurs with a EC$_{50}$ of 580 nM and 16 nM respectively, which corresponds to a relative potency of 0.03 for Decapeptide No. 2 with respect to the reference ANP-(103-126). This finding is consistent with the relative potency of 0.04 for vasorelaxant activity of Decapeptide No. 2 reported in Table II.

Guanylate Cyclase Determinations

Guanylate cyclase activity of rabbit lung membranes was assayed by the method of Waldman et al (vide supra). The incubation mixture consisted of 50 mM Tris pH 7.6, 10 mM theophylline, 2 mM isobutylmethylxanthine, 15 mM creatine phosphate, 20 mg (135 units/mg) creatine phosphokinase, and 100 μg of membrane protein in a final volume of 0.1 ml. The incubation was carried out at 37° C. The reaction was initiated by the addition of 1 mM GTP and 4 mM MgCl$_2$, and terminated with 0.9 ml of 50 mM sodium acetate, pH 4.0, followed by boiling for 3 minutes Cyclic GMP was assayed using the New England Nuclear radioimmunoassay kit.

C2—Effect of Peptide No. 2 on cGMP Production in Isolated Rat or Rabbit Aorta Isolated rat and rabbit aorta segments were incubated with ANP-(103-126) (20nM) under conditions which result in a maximal response in the production of cGMP. Peptide No. 2, which binds to the VR receptor was incubated under conditions identical to the control at two concentrations. The results from replicate experiments using different aorta segments are shown in Table III. The decapeptide 2 was able to raise the concentration of cGMP in both species. In the rat, 5 μM of Peptide 2 raised the cGMP production about 45 times above control concentration.

The following protocol was used to generate cyclic GMP in rat/rabbit aortic tissue. The thoracic aorta of male Sprague-Dawley rats or of rabbits was surgically removed and placed in a beaker of oxygenated Krebs-Bicarbonate buffer, pH 7.4. The tissue was cleaned of fat and blood and each aorta was cut into two 10 mm segments. Each of these 10 mm segments was longitudinally split, thus yielding four segments per thoracic aorta. The segments or aorta, each weighing approximately 600-800 micrograms, were preincubated for 30 minutes in a small petri dish containing the following:

3 ml oxygenated Krebs-Bicarbonate buffer
$2 \times 10^{-5}$ mM Norepinephrine
0.1 mM Isobutylmethylxanthine All incubations were done in a Forma Incubator at 37° C. under atmosphere of 95% $O_2$ and 5% $CO_2$. After he pre-incubation, 20 nM ANP-(103-126) was added to the appropriate segment, the test peptide of the invention was added to the companion segments. For each rat one of the four segments was used as the Control, one segment was used for the Standard 20 nM ANP-(103-126) and two segments were used for the test peptide. The incubation period for the stimulation of cyclic GMP in the presence of ANP-(103-126) was 30 minutes.

Following the incubation, the tissue segments were removed and frozen on dry-ice, the segments were then weighed and placed in test tubes for extraction with absolute ethanol. The tissues were homogenized with the Polytron and then centrifuged at 3000 rpm for 15 minutes at 4° C. The supernatant was poured off into another set of tubes and evaporated to dryness in a vacuum oven. After the tubes were dry, the samples were taken up in 2 ml 0.05 M sodium acetate buffer, pH 6.2. One hundred microliters of each extract was used for assay in the radioimmunoassay (NEN RIA Kit, $^{125}I$ tracer).

TABLE III

Effect of Peptide No. 2 on cGMP Levels in Isolated Aortae

| | Rabbit Aortae (n = 3) (pMol/gww) | |
|---|---|---|
| Control | 20 nM ANP-(103-126) | 1 uM Peptide 2 |
| 5.08 | 10.82 | 6.59 |
| 0.67 | 7.61 | 5.66 |
| 4.07 | 13.52 | 10.37 |
| 3.27 | 10.65 | 7.54 |
| (+/−1.34) | (+/−1.71) | (+/1-1.44) |

| | Rat Aortae (n = 2) (pMol/gww) | |
|---|---|---|
| Control | 20 nM ANP-(103-126) | 5 uM Peptide 2 |
| 0.32 | 9.52 | 13.15 |
| 0.33 | 14.71 | 14.05 |

D. Effect of Peptide No. 2 on Mean Arterial Pressure of Anesthetized Rats

Figure 4:
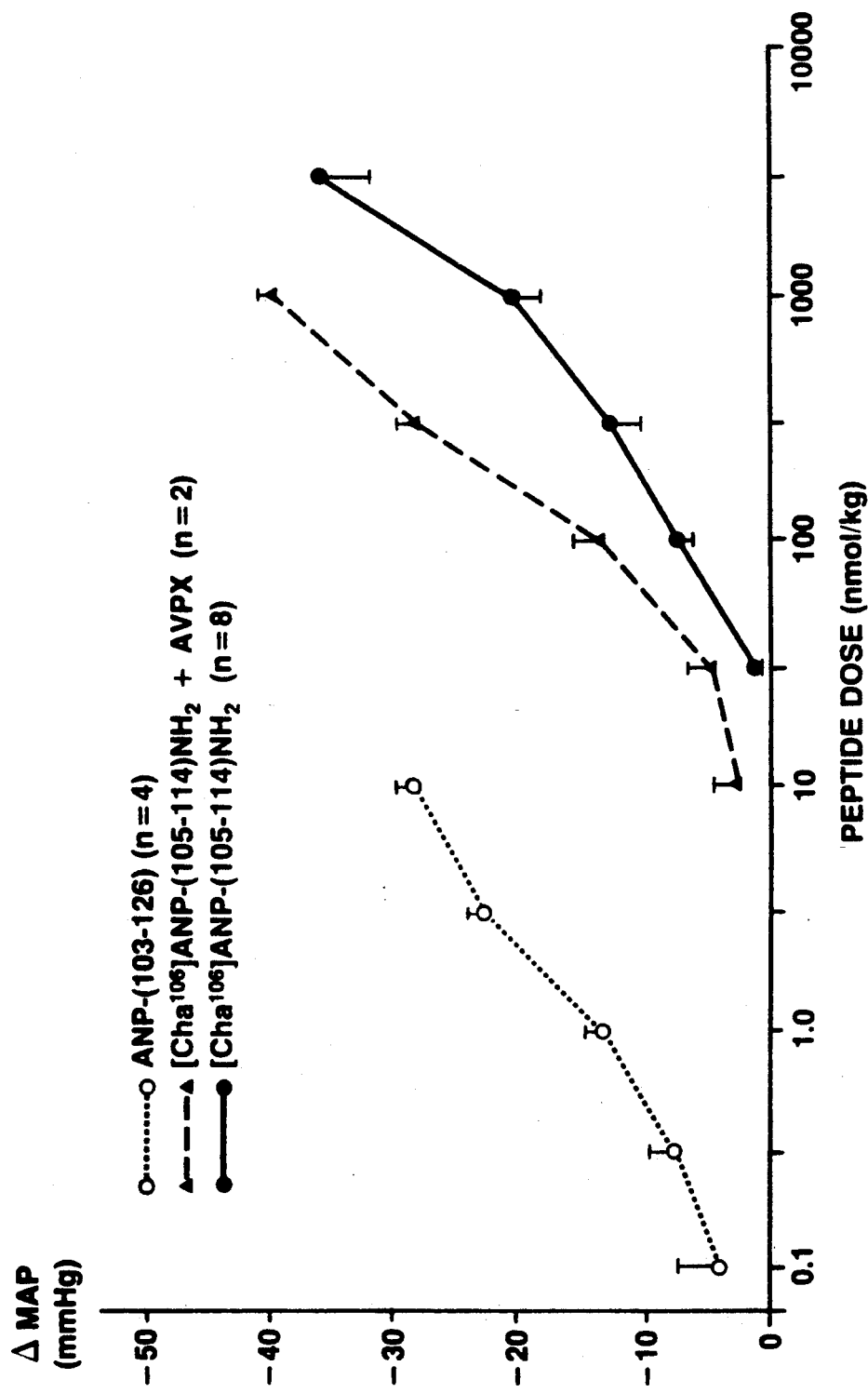
FIG. 4 shows decrease in arterial blood pressure (expressed in mm Hg) upon bolus injection of various doses of ANP-(103-126), of Peptide No. 2 {[Cha$^{106}$]ANP-(105-174)NH$_2$} and of Peptide No. 2 in combination with a vasopressin antagonist.

I.V. administration of Peptide No. 2 to anesthetized rats caused a dose dependent effect on mean arterial pressure, followed by a return to a pressure level higher than observed prior to I.V. administration of Peptide No. 2. Treatment with vasopressin ($V_1$) antagonist (Argenine-vasporessin antagonist; "Arg-VPX"; "AVPX" resulted in a prolongation of the decrease in mean arterial pressure (FIG. 4).

Depressor Activity of Peptide No. 2 In Vivo

Male Sprague-Dawley rats were anesthetized with Inactin (100 mg/kg, i.v.; Byk Gulden Konstanz) and instrumented with catheters in the trachea (PE-205), femoral artery and femoral vein to maintain airway patency, determine mean arterial pressure (MAP) and administer compounds, respectively. Following instrumentation, the rats were treated with mecamylamine (3 mg/kg, i.v.) and atropine (400 μg/kg, i.v.) to block autonomic neuro-transmission, and methoxamine (5-22 μg/kg/min) was infused to regulate MAP at 110-120 mmHg. The depressor activity of ANP (103-126) and Peptide No. 2 was evaluated to i.v. doses (bolus) of 0.1-10 nM/kg and 10-3000 nM/kg, respectively. Arterial pressure responses to the test compounds were monitored by connecting the femoral artery catheter to a Gould P23 pressure transducer which was coupled to a Gould pressure processor amplifier. MAP signals were displayed on a Gould 2800S recorder.

The results described above are consistent with the peptides of the invention acting as atrial naturetic peptide agonists. Also, such peptides act either as a vasopressin agonist or stimulate the release of vasopressin.

Peptides of Formula I have been shown to have a high affinity (nanomolar range) for the guanylate cyclase coupled (or vasorelaxant) receptor. Such peptides act as an agonist at the receptor of atrial peptide as demonstrated by the ability of the peptide to stimulate the production of cGMP and to fully relax rabbit aorta rings precontracted with norepinephrine.

In accord with these observations these peptides lower mean arterial blood pressure (MAP) upon infusion to anesthetized, mecamylamine treated rats. Such decrease in MAP may be prolonged by co-infusion of a vasopressin ($V_1$) antagonist. Peptide of Formula I may act to stimulate the release of vasopressin. As such, the compounds of the invention should be useful in treatment of hypertension especially in the case of patients suffering from the effects of diabetes insipidus, which disease is characterized by an impairment of vasopressin release. Also, this property of vasopressin release stimulation may be beneficial in treatment of normotensive patients suffering from diabetes insipidus. The peptides of the invention also represent a technical advance with respect to known atrial natriuretic peptide agonist compounds since such peptides of the invention are linear and much shorter and hence easier to produce than the cyclic (oxidized) conventional, much longer peptides, e.g., the 24-mer ANP-(103-126) or the 28-mer ANP-(99-126).

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A suitable dose can be administered, in multiple sub-doses per day. These sub-doses may be administered in unit dosage forms Typically, a dose or sub-dose may contain from about 1 mg to about 100 mg of active compound per unit dosage form.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound is such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral, e.g. intravenous, administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

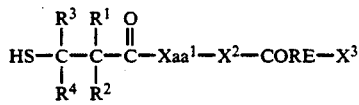

wherein each of $R^1$ and $R^2$ is independently selected from H, $NH_2$, NH—CO—Alkyl, NH—$(Xaa)_n$ where Xaa is selected from the alpha amino acids Ser, Leu and Arg and n is an integer selected from 1 through 6; wherein each of $R^3$ and $R^4$ is independently selected from H and alkyl, or $R^3$ and $R^4$ together may form a cyclic group; wherein $Xaa^1$ is a non-aromatic hydrophobic amino acid with a side chain which can be a cyclic or polycyclic alkyl radical of three to about fifteen carbon atoms; wherein $X^2$ is selected from the dipeptide fragments Gly-Gly, Gly-Ala, Gly-D-Ala, Ala-Gly and D-Ala-Gly; wherein CORE designates a core pentapeptide sequence selected from Arg-Ile-Asp-Arg-Ile, Arg-Met-Asp-Arg-Ile, Arg-Ile-Glu-Arg-Ile and Lys-Ile-Asp-Arg-Ile; and wherein $X^3$ is selected from the free carboxylic acid of the CORE C-terminal amino acid, its pharmaceutically-acceptable ester, amide and salt, a glycine residue and its pharmaceutically-acceptable ester, amide and salt.

2. Compound of claim 1 wherein each of $R^1$ through $R^4$ is selected to provide a sulfhydryl-containing residue attached to $Xaa^1$, said residue selected from D-cysteine, L-cysteine, D-penicillamine and L-penicillamine residue; wherein $Xaa^1$ is selected from L-Cha and D-Cha; wherein $X^2$ is selected from the dipeptidic fragments Gly-Gly, Gly-Ala, Gly-D-Ala, Ala-Gly and D-Ala-Gly; wherein the CORE pentapeptide is the sequence Arg-Ile-Asp-Arg-Ile; and wherein $X^3$ is selected from the free carboxylic acid of the CORE C-terminal amino acid, its pharmaceutically-acceptable ester, amide and salt, a glycine residue and its pharmaceutically-acceptable ester, amide and salt.

3. Compound of claim 2 selected from the group consisting of
Cys-Cha-Gly-Gly-Arg-Ile-Asp-Arg-Ile-GlyNH$_2$;
Cys-Cha-Gly-Gly-Arg-Ile-Asp-Arg-IleNH$_2$;
Cys-Cha-Gly-Gly-Lys-Ile-Asp-Arg-Ile-GlyNH$_2$;
Cys-Cha-Gly-Gly-Arg-Met-Asp-Arg-Ile-GlyNH$_2$;
Cys-Cha-Gly-Gly-Arg-Ile-Glu-Arg-Ile-GlyNH$_2$;
Cys-Cha-Gly-Gly-Arg-Met-Glu-Arg-Ile-GlyNH$_2$;
Cys-Cha-D-Ala-Gly-Arg-Ile-Asp-Arg-Ile-GlyNH$_2$;
Cys-Cha-Gly-D-Ala-Arg-Ile-Asp-Arg-Ile-GlyNH$_2$;
D-Pen-Cha-Gly-Gly-Arg-Ile-Asp-Arg-Ile-GlyNH$_2$;
L-Pen-Cha-Gly-Gly-Arg-Ile-Asp-Arg-Ile-GlyNH$_2$;
D-Cys-Cha-D-Ala-Gly-Arg-Ile-Asp-Arg-Ile-GlyNH$_2$;
D-Cys-Cha-Gly-Gly-Lys-Ile-Asp-Arg-Ile-GlyNH$_2$;
D-Cys-Cha-Gly-Gly-Arg-Ile-Asp-Arg-Ile-GlyNH$_2$;
D-Cys-Cha-Gly-Gly-Arg-Ile-Glu-Arg-Ile-GlyNH$_2$;
D-Cys-Cha-Gly-Gly-Arg-Met-Glu-Arg-Ile-GlyNH$_2$;
D-Pen-Cha-Gly-Gly-Arg-Met-Asp-Arg-Ile-GlyNH$_2$;
L-Pen-Cha-Gly-Gly-Arg-Met-Asp-Arg-Ile-GlyNH$_2$;
Cys-Cha-Gly-Gly-Lys-Ile-Asp-Arg-IleNH$_2$;
Cys-Cha-Gly-Gly-Arg-Met-Asp-Arg-IleNH$_2$;
Cys-Cha-Gly-Gly-Arg-Ile-Glu-Arg-IleNH$_2$;
Cys-Cha-Gly-Gly-Arg-Met-Glu-Arg-IleNH$_2$;
Cys-Cha-D-Ala-Gly-Arg-Ile-Asp-Arg-IleNH$_2$;
Cys-Cha-Gly-D-Ala-Arg-Ile-Asp-Arg-IleNH$_2$;
D-Pen-Cha-Gly-Gly-Arg-Ile-Asp-Arg-IleNH$_2$;
L-Pen-Cha-Gly-Gly-Arg-Ile-Asp-Arg-IleNH$_2$;
D-Cys-Cha-D-Ala-Gly-Arg-Ile-Asp-Arg-IleNH$_2$;
D-Cys-Cha-Gly-Lys-Ile-Asp-Arg-IleNH$_2$;
D-Cys-Cha-Gly-Gly-Arg-Met-Asp-Arg-IleNH$_2$;
D-Cys-Cha-Gly-Gly-Arg-Ile-Glu-Arg-IleNH$_2$;
D-Cys-Cha-Gly-Gly-Arg-Met-Glu-Arg-IleNH$_2$;
D-Pen-Cha-Gly-Gly-Arg-Met-Asp-Arg-IleNH$_2$; and
L-Pen-Cha-Gly-Gly-Arg-Met-Asp-Arg-IleNH$_2$.

4. Compound of claim 3 selected from the group consisting of
Cys-Cha-Gly-Gly-Arg-Ile-Asp-Arg-Ile-GlyNH$_2$;
D-Cys-Cha-Gly-Gly-Arg-Ile-Asp-Arg-Ile-GlyNH$_2$;
L-Pen-Cha-Gly-Gly-Arg-Ile-Asp-Arg-Ile-GlyNH$_2$; and
Cys-Cha-Gly-Gly-Arg-Ile-Asp-Arg-IleNH$_2$.

5. A pharmaceutical-composition comprising one or more active ingredients and a pharmaceutically-acceptable carrier or diluent, one of said active ingredients being a compound selected from a family of compounds of the formula

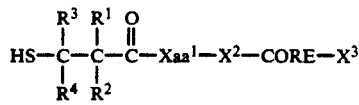

wherein each of $R^1$ and $R^2$ is independently selected from H, $NH_2$, NH—CO—Alkyl, NH—$(Xaa)_n$ where Xaa is selected from the alpha amino acids Ser, Leu and Arg and n is an integer selected from 1 through 6; wherein each of $R^3$ and $R^4$ is independently selected from H and alkyl, or $R^3$ and $R^4$ together may form a cyclic group; wherein $Xaa^1$ is a non-aromatic hydrophobic amino acid with a side chain which can be a cyclic or polycyclic alkyl radical of three to about fifteen carbon atoms; wherein $X^2$ is selected from the dipeptide fragments Gly-Gly, Gly-Ala, Gly-D-Ala, Ala-Gly and D-Ala-Gly; wherein CORE designates a core pentapeptide sequence selected from Arg-Ile-Asp-Arg-Ile, Arg-Met-Asp-Arg-Ile, Arg-Ile-Glu-Arg-Ile and Lys-Ile-Asp-Arg-Ile; and wherein $X^3$ is selected from the free carboxylic acid of the CORE C-terminal amino acid, its pharmaceutically-acceptable ester, amide and salt, a glycine residue and its pharmaceutically-acceptable ester, amide and salt.

6. The composition of claim 5 wherein each of $R^1$ through $R^4$ is selected to provide a sulfhydryl-containing residue attached to $Xaa^1$, said residue selected from D-cysteine, L-cysteine, D-penicillamine and L-penicillamine residue; wherein $Xaa^1$ is selected from L-Cha and D-Cha; wherein $X^2$ is selected from the dipeptidic fragments Gly-Gly, Gly-Ala, Gly-D-Ala, Ala-Gly and D-Ala-Gly; wherein the CORE pentapeptide is the sequence Arg-Ile-Asp-Arg-Ile; and wherein $X^3$ is selected from the free carboxylic acid of the CORE C-terminal amino acid, its pharmaceutically-acceptable ester, amide and salt, a glycine residue and its pharmaceutically-acceptable ester, amide and salt.

7. The composition of claim 6 wherein said compound is selected from the group consisting of
Cys-Cha-Gly-Gly-Arg-Ile-Asp-Arg-Ile-GlyNH$_2$;
Cys-Cha-Gly-Gly-Arg-Ile-Asp-Arg-IleNH$_2$;
Cys-Cha-Gly-Gly-Lys-Ile-Asp-Arg-Ile-GlyNH$_2$;
Cys-Cha-Gly-Gly-Arg-Met-Asp-Arg-Ile-GlyNH$_2$;
Cys-Cha-Gly-Gly-Arg-Ile-Glu-Arg-Ile-GlyNH$_2$;
Cys-Cha-Gly-Gly-Arg-Met-Glu-Arg-Ile-GlyNH$_2$;
Cys-Cha-D-Ala-Gly-Arg-Ile-Asp-Arg-Ile-GlyNH$_2$;
Cys-Cha-Gly-D-Ala-Arg-Ile-Asp-Arg-Ile-GlyNH$_2$;
D-Pen-Cha-Gly-Gly-Arg-Ile-Asp-Arg-Ile-GlyNH$_2$;
L-Pen-Cha-Gly-Gly-Arg-Ile-Asp-Arg-Ile-GlyNH$_2$;
D-Cys-Cha-D-Ala-Gly-Arg-Ile-Asp-Arg-Ile-GlyNH$_2$;
D-Cys-Cha-Gly-Gly-Lys-Ile-Asp-Arg-Ile-GlyNH$_2$;
D-Cys-Cha-Gly-Gly-Arg-Ile-Asp-Arg-Ile-GlyNH$_2$;
D-Cys-Cha-Gly-Gly-Arg-Ile-Glu-Arg-Ile-GlyNH$_2$;
D-Cys-Cha-Gly-Gly-Arg-Met-Glu-Arg-Ile-GlyNH$_2$;
D-Pen-Cha-Gly-Gly-Arg-Met-Asp-Arg-Ile-GlyNH$_2$;
L-Pen-Cha-Gly-Gly-Arg-Met-Asp-Arg-Ile-GlyNH$_2$;
Cys-Cha-Gly-Gly-Lys-Ile-Asp-Arg-IleNH$_2$;
Cys-Cha-Gly-Gly-Arg-Met-Asp-Arg-IleNH$_2$;
Cys-Cha-Gly-Gly-Arg-Ile-Glu-Arg-IleNH$_2$;
Cys-Cha-Gly-Gly-Arg-Met-Glu-Arg-IleNH$_2$;
Cys-Cha-D-Ala-Gly-Arg-Ile-Asp-Arg-IleNH$_2$;
Cys-Cha-Gly-D-Ala-Arg-Ile-Asp-Arg-IleNH$_2$;
D-Pen-Cha-Gly-Gly-Arg-Ile-Asp-Arg-IleNH$_2$;
L-Pen-Cha-Gly-Gly-Arg-Ile-Asp-Arg-IleNH$_2$;
D-Cys-Cha-D-Ala-Gly-Arg-Ile-Asp-Arg-IleNH$_2$;
D-Cys-Cha-Gly-Gly-Lys-Ile-Asp-Arg-IleNH$_2$;
D-Cys-Cha-Gly-Gly-Arg-Met-Asp-Arg-IleNH$_2$;
D-Cys-Cha-Gly-Gly-Arg-Ile-Glu-Arg-IleNH$_2$;
D-Cys-Cha-Gly-Gly-Arg-Met-Glu-Arg-IleNH$_2$;
D-Pen-Cha-Gly-Gly-Arg-Met-Asp-Arg-IleNH$_2$; and L-Pen-Cha-Gly-Gly-Arg-Met-Asp-Arg-IleNH$_2$.

8. The composition of claim 7 wherein said compound is selected from the group consisting of
Cys-Cha-Gly-Gly-Arg-Ile-Asp-Arg-Ile-GlyNH$_2$;
D-Cys-Cha-Gly-Gly-Arg-Ile-Asp-Arg-Ile-GlyNH$_2$;
L-Pen-Cha-Gly-Gly-Arg-Ile-Asp-Arg-Ile-GlyNH$_2$; and
Cys-Cha-Gly-Gly-Arg-Ile-Asp-Arg-IleNH$_2$.

9. The composition of claim 8 further comprising as an active ingredient a vasopressin ($V_1$) antagonist.

10. The composition of claim 9 wherein said vasopressin ($V_1$) antagonist is arginine-vasopressin antagonist.

11. A therapeutic method for treating hypertension, said method comprising administering to a patient a therapeutically-effective amount of a compound of the formula

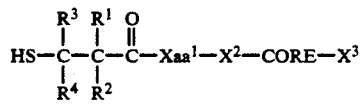

ps wherein each of $R^1$ and $R^2$ is independently selected from H, $NH_2$, NH—CO—Alkyl, NH—$(Xaa)_n$ where Xaa is selected from the alpha amino acids Ser, Leu and Arg and n is an integer selected from 1 through 6; wherein each of $R^3$ and $R^4$ is independently selected from H and alkyl, or $R^3$ and $R^4$ together may form a cyclic group; wherein $Xaa^1$ is a non-aromatic hydrophobic amino acid with a side chain which can be a cyclic or polycyclic alkyl radical of three to about fifteen carbon atoms; wherein $X^2$ is selected from the dipeptide fragments Gly-Gly, Gly-ala, Gly-D-Ala, Ala-Gly and D-Ala-Gly; wherein CORE designates a core pentapeptide sequence selected from Arg-Ile-Asp-Arg-Ile, Arg-Met-Asp-Arg-Ile, Arg-Ile-Glu-Arg-Ile and Lys-Ile-Asp-Arg-Ile; and wherein $X^3$ is selected from the free carboxylic acid of the CORE C-terminal amino acid, its pharmaceutically-acceptable ester, amide and salt, a glycine residue and its pharmaceutically-acceptable ester, amide and salt.

12. The method of claim 11 wherein each of $R^1$ through $R^4$ is selected to provide a sulfhydryl-containing residue attached to $Xaa^1$, said residue selected from D-cysteine, L-cysteine, D-penicillamine and L-penicillamine residue; wherein $Xaa^1$ is selected from L-Cha and D-Cha; wherein $X^2$ is selected from the dipeptidic fragments Gly-Gly, Gly-Ala, Gly-D-Ala, Ala-Gly and D-Ala-Gly; wherein the CORE pentapeptide is the sequence Arg-Ile-Asp-Arg-Ile; and wherein $X^3$ is selected form the free carboxylic acid of the CORE C-terminal amino acid, its pharmaceutically-acceptable ester, amide and salt, a glycine residue and its pharmaceutically-acceptable ester, amide and salt.

13. The method of claim 12 wherein said compound is selected from the group consisting of
Cys-Cha-Gly-Gly-Arg-Ile-Asp-Arg-Ile-GlyNH$_2$;
Cys-Cha-Gly-Gly-Arg-Ile-Asp-Arg-IleNH$_2$;
Cys-Cha-Gly-Gly-Lys-Ile-Asp-Arg-Ile-GlyNH$_2$;
Cys-Cha-Gly-Gly-Arg-Met-Asp-Arg-Ile-GlyNH$_2$;
Cys-Cha-Gly-Gly-Arg-Ile-Glu-Arg-Ile-GlyNH$_2$;
Cys-Cha-Gly-Gly-Arg-Met-Glu-Arg-Ile-GlyNH$_2$;
Cys-Cha-D-Ala-Gly-Arg-Ile-Asp-Arg-Ile-GlyNH$_2$;
Cys-Cha-Gly-D-Ala-Arg-Ile-Asp-Arg-Ile-GlyNH$_2$;
D-Pen-Cha-Gly-Gly-Arg-Ile-Asp-Arg-Ile-GlyNH$_2$;
L-Pen-Cha-Gly-Gly-Arg-Ile-Asp-Arg-Ile-GlyNH$_2$;

D-Cys-Cha-D-Ala-Gly-Arg-Ile-Asp-Arg-Ile-GlyNH$_2$;
D-Cys-Cha-Gly-Gly-Lys-Ile-Asp-Arg-Ile-GlyNH$_2$;
D-Cys-Cha-Gly-Gly-Arg-Ile-Asp-Arg-Ile-GlyNH$_2$;
D-Cys-Cha-Gly-Gly-Arg-Ile-Glu-Arg-Ile-GlyNH$_2$;
D-Cys-Cha-Gly-Gly-Arg-Met-Glu-Arg-Ile-GlyNH$_2$;
D-Pen-Cha-Gly-Gly-Arg-Met-Asp-Arg-Ile-GlyNH$_2$;
L-Pen-Cha-Gly-Gly-Arg-Met-Asp-Arg-Ile-GlyNH$_2$;
Cys-Cha-Gly-Gly-Lys-Ile-Asp-Arg-IleNH$_2$;
Cys-Cha-Gly-Gly-Arg-Met-Asp-Arg-IleNH$_2$;
Cys-Cha-Gly-Gly-Arg-Ile-Glu-Arg-IleNH$_2$;
Cys-Cha-Gly-Gly-Arg-Met-Glu-Arg-IleNH$_2$;
Cys-Cha-D-Ala-Gly-Arg-Ile-Asp-Arg-IleNH$_2$;
Cys-Cha-Gly-D-Ala-Arg-Ile-Asp-Arg-IleNH$_2$;
D-Pen-Cha-Gly-Gly-Arg-Ile-Asp-Arg-IleNH$_2$;
L-Pen-Cha-Gly-Gly-Arg-Ile-Asp-Arg-IleNH$_2$;
D-Cys-Cha-D-Ala-Gly-Arg-Ile-Asp-Arg-IleNH$_2$;
D-Cys-Cha-Gly-Gly-Lys-Ile-Asp-Arg-IleNH$_2$;
D-Cys-Cha-Gly-Gly-Arg-Met-Asp-Arg-IleNH$_2$;
D-Cys-Cha-Gly-Gly-Arg-Ile-Glu-Arg-IleNH$_2$;
D-Cys-Cha-Gly-Gly-Arg-Met-Glu-Arg-IleNH$_2$;
D-Pen-Cha-Gly-Gly-Arg-Met-Asp-Arg-IleNH$_2$; and
L-Pen-Cha-Gly-Gly-Arg-Met-Asp-Arg-IleNH$_2$.

14. The method of claim 13 wherein said compound is selected from the group consisting of
Cys-Cha-Gly-Gly-Arg-Ile-Asp-Arg-Ile-GlyNH$_2$;
D-Cys-Cha-Gly-Gly-Arg-Ile-Asp-Arg-Ile-GlyNH$_2$;
L-Pen-Cha-Gly-Gly-Arg-Ile-Asp-Arg-Ile-GlyNH$_2$; and
Cys-Cha-Gly-Gly-Arg-Ile-Asp-Arg-IleNH$_2$.

* * * * *